(12) United States Patent
Li et al.

(10) Patent No.: US 12,180,146 B2
(45) Date of Patent: Dec. 31, 2024

(54) ANTIHYPERTENSIVE POLYOL COMPOUND AND DERIVATIVE THEREOF

(71) Applicant: TAO PHARMACEUTICAL (SUZHOU) CO., LTD, Jiangsu (CN)

(72) Inventors: Honglin Li, Shanghai (CN); Zhenjiang Zhao, Shanghai (CN); Rui Wang, Shanghai (CN); Yinchu Shen, Shanghai (CN); Jianjun Fu, Shanghai (CN); Yufang Xu, Shanghai (CN); Xuhong Qian, Shanghai (CN); Qian Jiao, Shanghai (CN); Shiliang Li, Shanghai (CN)

(73) Assignee: TAO PHARMACEUTICAL (SUZHOU) CO. LTD, Jiangsu (CN)

( * ) Notice: Subject to any disclaimer, the term of this patent is extended or adjusted under 35 U.S.C. 154(b) by 184 days.

(21) Appl. No.: 17/424,105

(22) PCT Filed: Jun. 12, 2020

(86) PCT No.: PCT/CN2020/095974
§ 371 (c)(1),
(2) Date: Jul. 19, 2021

(87) PCT Pub. No.: WO2020/249117
PCT Pub. Date: Dec. 17, 2020

(65) Prior Publication Data
US 2022/0098134 A1 Mar. 31, 2022

(30) Foreign Application Priority Data

Jun. 12, 2020 (CN) .......................... 201910507506.4

(51) Int. Cl.
C07C 33/26 (2006.01)
A61P 9/12 (2006.01)
(Continued)

(52) U.S. Cl.
CPC ................ *C07C 33/26* (2013.01); *A61P 9/12* (2018.01); *C07C 33/30* (2013.01); *C07C 43/23* (2013.01); *C07C 49/82* (2013.01); *C07C 69/16* (2013.01)

(58) Field of Classification Search
CPC ......... C07C 33/26; C07C 33/30; C07C 43/23; C07C 49/82; C07C 69/16; C07C 69/96;
(Continued)

(56) References Cited

U.S. PATENT DOCUMENTS 9,278,968 B2 3/2016 Kurosaki et al.
2013/0310332 A1* 11/2013 Barbeau ............... C07D 309/10
549/417

(Continued)

FOREIGN PATENT DOCUMENTS

CN 1369565 A 9/2002
CN 101302543 A 11/2008
(Continued)

OTHER PUBLICATIONS

Zhao et al., "Three new phenyl-ethanediols from the fruiting bodies of the mushroom Fomes fomentarius", 2013, Journal of Asian Natural Products Research, 15(3), pp. 310-314. (http://dx.doi.org/10.1080/10286020.2013.764519) (Year: 2013).*

(Continued)

*Primary Examiner* — Jeffrey S Lundgren
*Assistant Examiner* — Alexander K. Showalter
(74) *Attorney, Agent, or Firm* — Mintz Levin Cohn Ferris Glovsky and Popeo, P.C.

(57) ABSTRACT

The present invention provides a compound as represented by formula I, or a pharmaceutically acceptable salt or ester, a prodrug, an optical isomer, a stereoisomer, or a solvate thereof. The compound provided by the present invention (Continued)

can be used for preparing drugs for preventing or treating hypertension, or hypertension-related diseases, or pulmonary hypertension, or pulmonary hypertension-related diseases. The compound provided by the present invention has a different mechanism from existing drugs for treating hypertension and pulmonary hypertension, thereby laying a new material foundation for the development of drugs for treating hypertension and pulmonary hypertension.

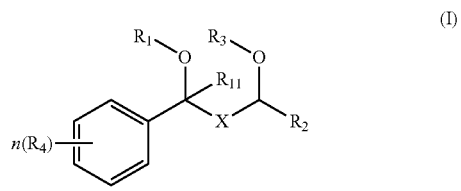

(I)

3 Claims, 3 Drawing Sheets

(51) Int. Cl.
C07C 33/30 (2006.01)
C07C 43/23 (2006.01)
C07C 49/82 (2006.01)
C07C 69/16 (2006.01)

(58) Field of Classification Search
CPC ... C07C 215/30; C07C 215/68; C07C 215/78; C07C 229/14; C07C 271/12; C07C 33/46; A61P 9/12; A61P 3/04; A61P 3/10; A61P 9/00; A61P 11/00; A61P 13/00; A61P 13/12; A61P 19/10; A61P 27/06; A61K 31/047; A61K 31/05; A61K 31/075; A61K 31/085; A61K 31/122; A61K 31/136; A61K 31/192; A61K 31/197; A61K 31/216; A61K 31/27; A61K 31/336; A61K 31/353; A61K 31/7048; A61K 31/137; A61K 31/22; A61K 31/343; A61K 31/357; A61K 31/381; A61K 31/403; A61K 31/404; A61K 31/428; A61K 31/47; A61K 31/661; A61K 31/665; A61K 31/7034; A61K 31/12; A61K 31/195; A61K 31/325; A61K 31/352; A61K 31/7032; C07D 209/08; C07D 311/30; C07D 311/32; C07D 311/62; C07D 317/36; C07D 317/54; C07D 319/18; C07D 333/16; C07D 417/04; C07H 15/18

See application file for complete search history.

(56) References Cited

U.S. PATENT DOCUMENTS

2015/0232464 A1 8/2015 Kurosaki
2016/0143930 A1* 5/2016 Quintela Fernandez ............. A61P 43/00 514/557

FOREIGN PATENT DOCUMENTS

CN 104822680 A 8/2015
KR 10-2015-0130134 A 11/2015
WO 2019040107 A1 2/2019

OTHER PUBLICATIONS

Paulson, Cerebral Apoplexy (Stroke): Pathogenesis, Pathophysiology and Therapy as Illustrated by Regional Blood Flow Measurements in the Brainâ, Stroke, 2, pp. 327-360 (Year: 1971).*
Paulson, "Cerebral Apoplexy (Stroke): Pathogenesis, Pathophysiology and Therapy as Illustrated by Regional Blood Flow Measurements in the Brain", Stroke, vol. 2, pp. 327-360 (Year: 1971).*
International Search Report mailed Apr. 10, 2020 corresponding to PCT/CN/2020/095974 filed Sep. 4, 2020; 4 pages.
Aratikatla, Eswar K. et al., "Norepinephrine alkaloids as antiplasmodial agents: Synthesis of syncarpamide and insight into the structure-activity relationships of its analogues as antiplasmodial agents," *European Journal of Medicinal Chemistry* (Jul. 25, 2017) 138:1089-1105.
Yang, Wan-Qiu et al., "New phenyl-ethanediols from the culture broth of Boletus edulis," *Journal of Basic Microbiology* (Dec. 31, 2007) 47:191-193.
Yang, Xueqiong et al., "A Novel Tetrahydrofuranyl Fatty Acid from a New Microbial Isolate, *Pestalotia* sp. YIM 69032 Cultivated in Extract of Potato," *J Am Oil Chem Soc.* (2013; published online Sep. 18, 2012) 90:159-162.
Bobik, Alex et al., "Evidence for a Predominantly Central Hypotensive Effect of a-Methyldopa in Humans", Hypertension, vol. 8, No. 1, Jan. 1, 1986, pp. 16-23.

* cited by examiner

ANTIHYPERTENSIVE POLYOL COMPOUND AND DERIVATIVE THEREOF

TECHNICAL FIELD

The present invention relates to the field of pharmaceutical chemistry; in particular, the present invention relates to an antihypertensive polyol compound, derivatives thereof, and their use in the preparation of antihypertensive drugs.

BACKGROUND

Hypertension is the most common cardiovascular disease in the world. Although some hypertension patients have genetic susceptibility, environmental factors are non-negligible pathogenic factors. As the quality of life is improved and the eating habits of people are changed, the incidence of diseases, such as hyperlipidemia, atherosclerosis and the like is continuously increased, and the incidence rate of hypertension is gradually increased. Hypertension is a guidewire of a variety of diseases, which increases the risk of disease in coronary heart disease, heart failure, and kidney. Therefore, lowering blood pressure is a key to hypertension treatment. The purpose of the treatment of hypertension is to control the blood pressure, reduce the target organ damage and the incidence of cardiovascular disease, the death rate, and improve long-term prognosis and quality of life. To achieve this, drug therapy is also required in addition to improving lifestyle.

Currently, clinically commonly used anti-hypertension drugs are classified to the following types: riuretic antihypertensive drug, β receptor blocker, calcium antagonist (CCB), angiotensin converting enzyme inhibitor (ACEI), angiotensin II receptor blocker (ARB), α receptor blocker. While the above-mentioned drugs can effectively reduce hypotension, there are significant side effects, such as water, electrolyte disorders, asthma, heart rate-slowing, sexual dysfunction, etc. In addition, patients often suffer from drug dependence, and once the drug is stopped, blood pressure will rebound immediately.

Pulmonary high pressure (PAH) is another disease severely compromising human life safety. The diagnostic criterion of PAH is that in resting state, the resulting average pulmonary artery pressure (Maculoy) is ≥25 mmg/g detected by right-cardiac catheter method. The onset of PAH is caused by a variety of factors, including dysfunction of pulmonary artery endothelial cells (PAEC), abnormal proliferation and reconstruction of pulmonary artery endothelial cells and pulmonary artery smooth muscle cells (PASMC), and in situ formation of thrombus. PAH is a disease of high mortality, poor prognosis and average survival time of only 2.8 years, and has become a major class of cardiovascular disease in Western countries. In the occurence and development of PAH, the pathways, such as endothelin (ET-1), NO and prost, play an important role. For the three targets, the currently marketed PAH therapeutic drugs are primarily endothelin receptor antagonist bosentan, tambosentan, bubebactam, and the like, 5-phosphodiesterase (PDE5) inhibitors sildenafil, taddenafil, valenafil, and the like, and alprost analogs Ealprost, Iloprost, Triprost and the like. Although these drugs have certain alleviation effects on the development of PAH disease, the disease in the patient typically deteriorates. Studies indicate that the survival rate of 5 years of patients is still only about 50%. In addition, many PAH patients tend to burden high drug costs due to long-term administration, and patients with severe illness also need a combination of multiple drugs to control the disease, which causes heavier economic pressure to patients and society, and severely reduces the cure rate of patients. Therefore, it is of important significance to find new targeting drugs that can inhibit or even reverse the development of pulmonary hypertension for improving the prognosis and life quality of PAH patients.

Therefore, the research and development of therapeutic agents for hypertension, pulmonary hypertension and related diseases can still have extremely important clinical significance and application prospects.

SUMMARY OF THE INVENTION

It is an object of the present invention to provide a novel compound that can be used as a medicament for hypertension, pulmonary hypertension and associated diseases thereof.

In a first aspect, the present invention provides the use of a compound of formula I, or a pharmaceutically acceptable salt or ester, prodrug, optical isomer, stereoisomer, or solvate thereof in the preparation of a medicament for preventing or treating hypertension or hypertension related diseases or pulmonary hypertension or pulmonary hypertension related diseases,

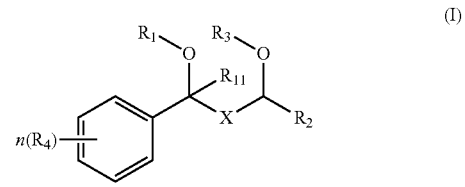

wherein,

X is absent or a substituted or unsubstituted C1-C3 linear or branched alkyl;

n is an integer of 0-5, preferably an integer of 1-5;

$R_1$ and $R_3$ are each independently selected from H, D, a substituted or unsubstituted C1-C10 alkyl, substituted or unsubstituted —$(CH_2CH_2O)_mH$, substituted or unsubstituted benzyl, substituted or unsubstituted phenyl, substituted or unsubstituted C1-C5 alkyl formyl, substituted or unsubstituted benzoyl, substituted or unsubstituted aminoacetyl, substituted or unsubstituted

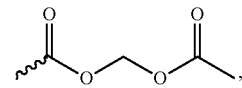

substituted or unsubstituted

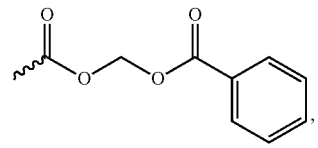

substituted or unsubstituted monosaccharide, disaccharide or polysaccharide group or substituted or unsubstituted phosphate group, where m is an integer of 0-5, preferably 0-3, most preferably 1-2; or $R_1$ and $R_3$ can form a five-membered ring

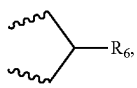

where $R_6$ is a substituted or unsubstituted C1-C5 alkyl;

$R_2$ and $R_{11}$ are each independently selected from H, D, a carbonyl, substituted or unsubstituted C1-C10 alkyl, substituted or unsubstituted phenyl, $CH_2OR_7$; $R_7$ is selected from H, a substituted or unsubstituted C1-C10 alkyl, substituted or unsubstituted monosaccharide, disaccharide or polysaccharide group;

$R_4$ is selected from H, D, a substituted or unsubstituted C1-C10 linear or branched alkyl, substituted or unsubstituted C1-C10 unsaturated linear or branched alkyl, hydroxyl, substituted or unsubstituted C1-C10 alkoxy, halogen, substituted or unsubstituted benzyl, substituted or unsubstituted phenyl, substituted or unsubstituted C1-C5 alkylformyl, substituted or unsubstituted benzoyl, nitro, COOH, substituted or unsubstituted C1-C5 alkoxyformyl, amino, substituted or unsubstituted C1-C5 alkylamino, substituted or unsubstituted C1-C5 alkylcarboxamido, substituted or unsubstituted benzoylamino, substituted or unsubstituted benzo-aromatic ring or five-membered or six-membered heterocyclic ring containing heteroatoms.

In a preferred embodiment, the phosphate group is as shown in

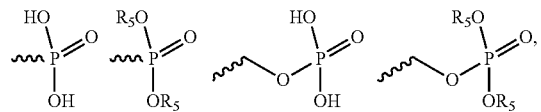

wherein $R_5$ is selected from a substituted or unsubstituted C1-C10 alkyl.

In a preferred embodiment, the substituted or unsubstituted aminoacetyl is as shown in

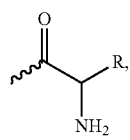

wherein R is various amino acid substituents.

In a specific embodiment, the compound is shown in Formula II

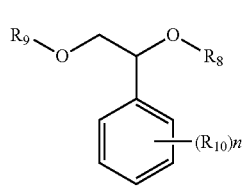

wherein, $R_8$ is selected from H, a substituted or unsubstituted C1-C10 alkyl, substituted or unsubstituted benzyl, substituted or unsubstituted C1-C5 alkylformyl, substituted or unsubstituted benzoyl, substituted or unsubstituted aminoacetyl, or substituted or unsubstituted monosaccharide, disaccharide or polysaccharide group;

$R_9$ is selected from H, a substituted or unsubstituted C1-C10 alkyl, substituted or unsubstituted benzyl, substituted or unsubstituted C1-C5 alkylformyl, substituted or unsubstituted benzoyl, substituted or unsubstituted aminoacetyl, or substituted or unsubstituted monosaccharide, disaccharide or polysaccharide group;

$R_{10}$ is selected from H, a substituted or unsubstituted C1-C10 linear or branched alkyl, substituted or unsubstituted C1-C10 unsaturated linear or branched alkyl, F, Cl, Br, hydroxyl, C1-C3 linear or branched alkoxy, substituted or unsubstituted C1-C5 alkyl formyl, substituted or unsubstituted benzoyl, or substituted or unsubstituted benzo-aromatic ring or five-membered or six-membered heterocyclic ring containing heteroatom(s); and n is any integer selected from 0-3.

In a specific embodiment, the present invention provides the use of following compounds, or a salt or ester, prodrug, optical isomer or solvate thereof in the preparation of a medicament for preventing or treating hypertension or hypertension related diseases or pulmonary hypertension or pulmonary hypertension related diseases:

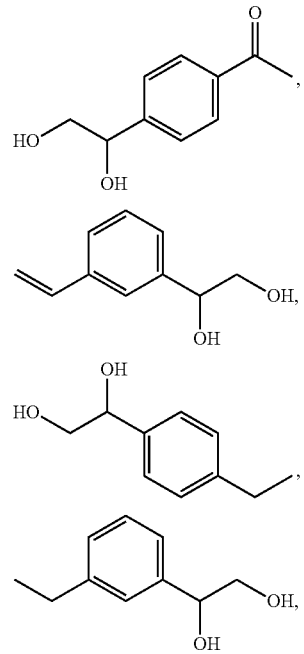

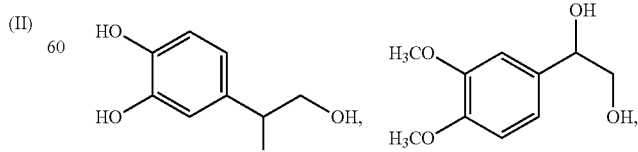

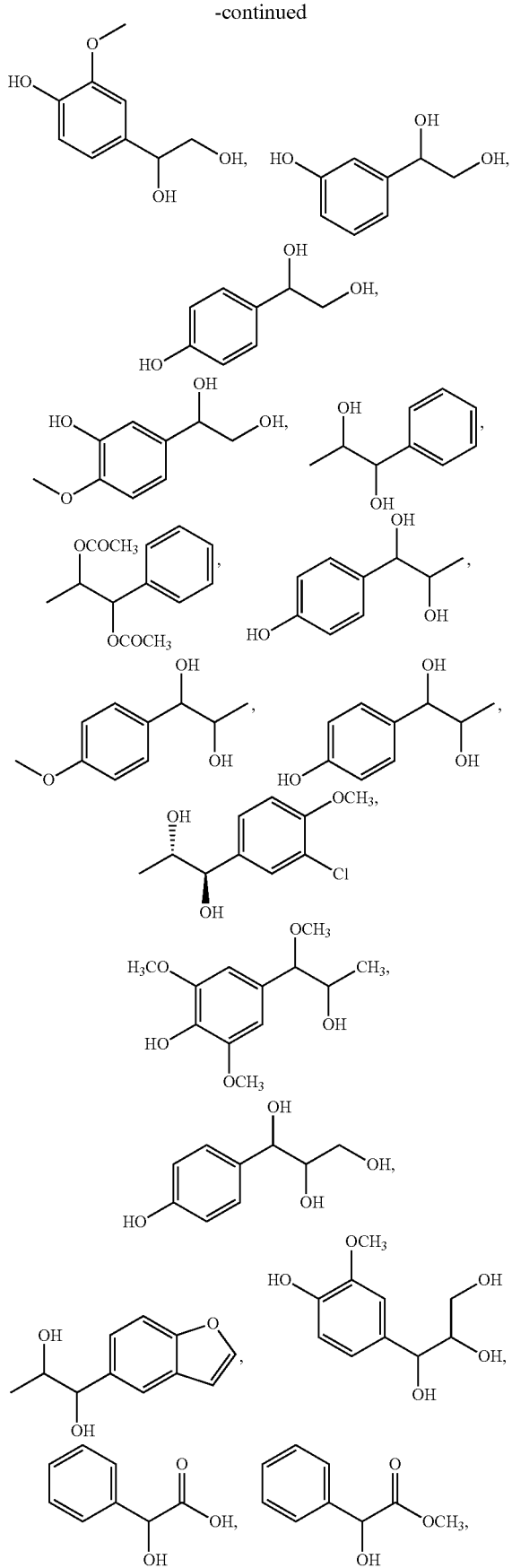
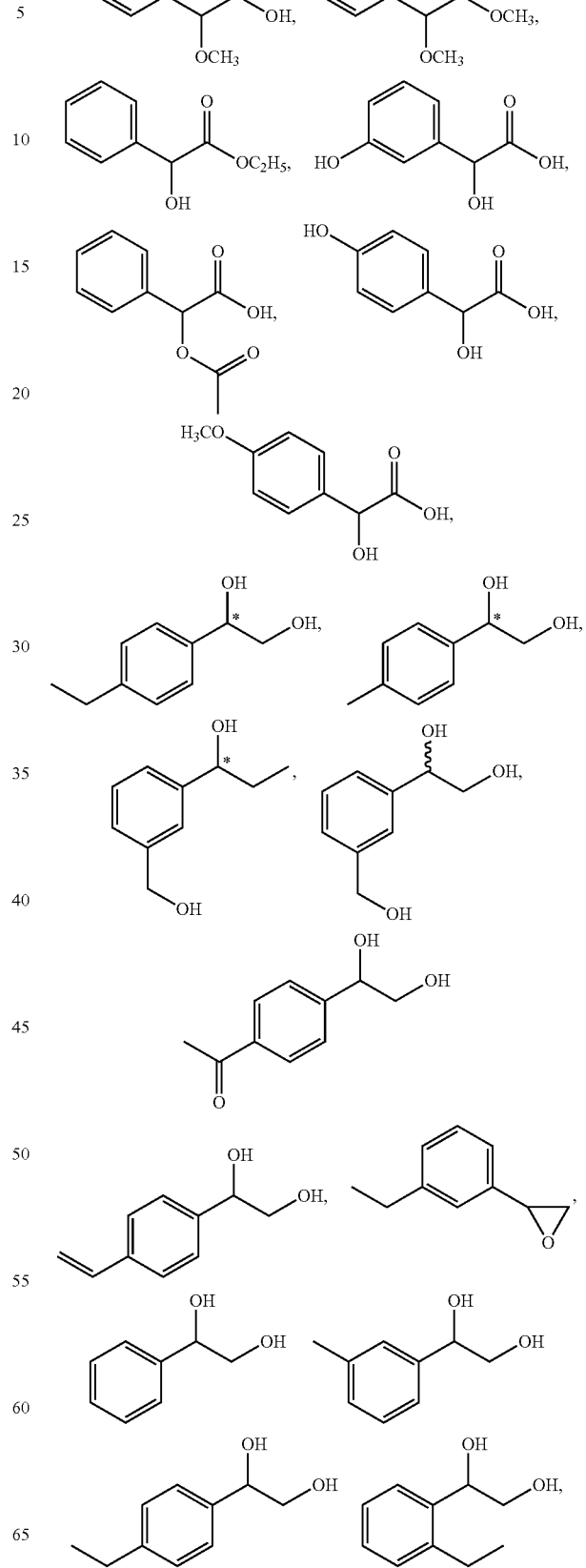

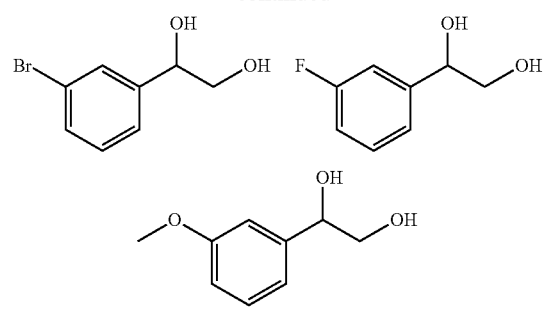
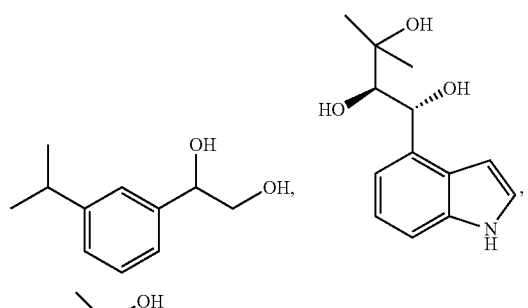
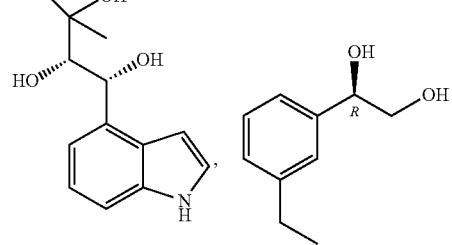
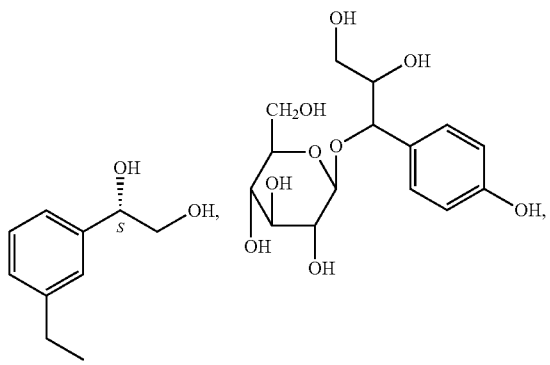
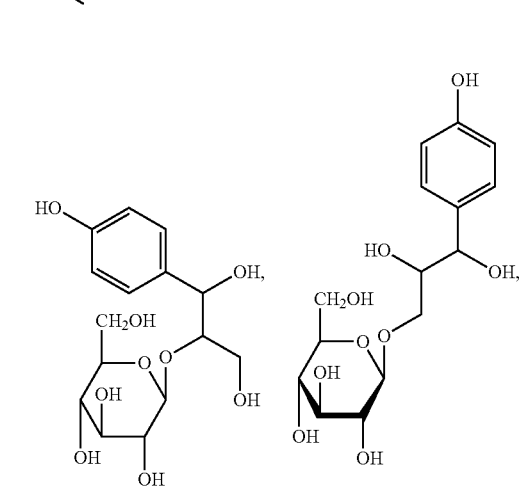
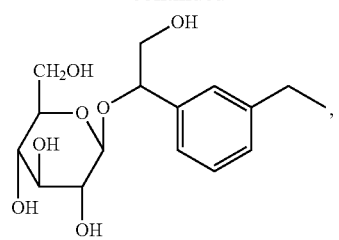
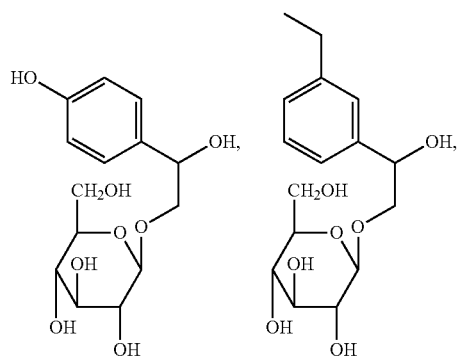
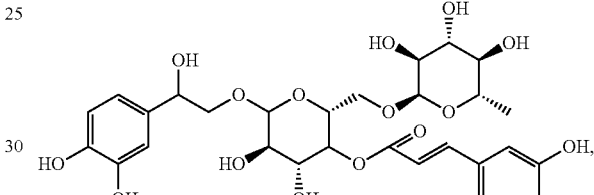
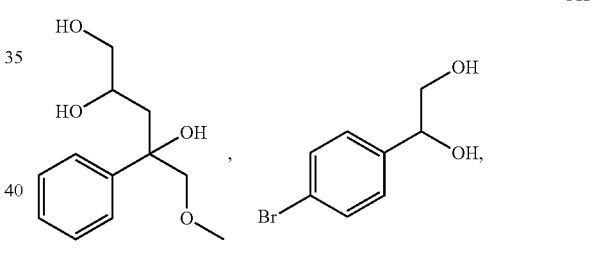
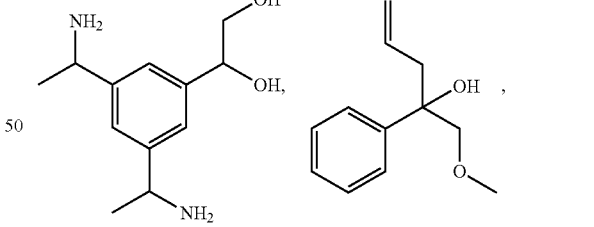
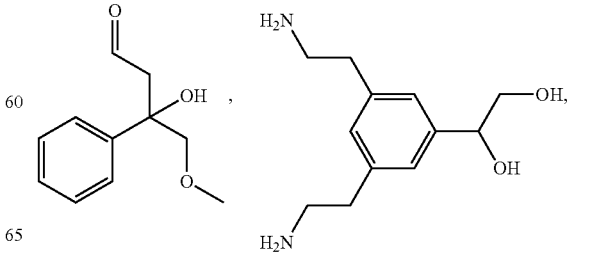

-continued
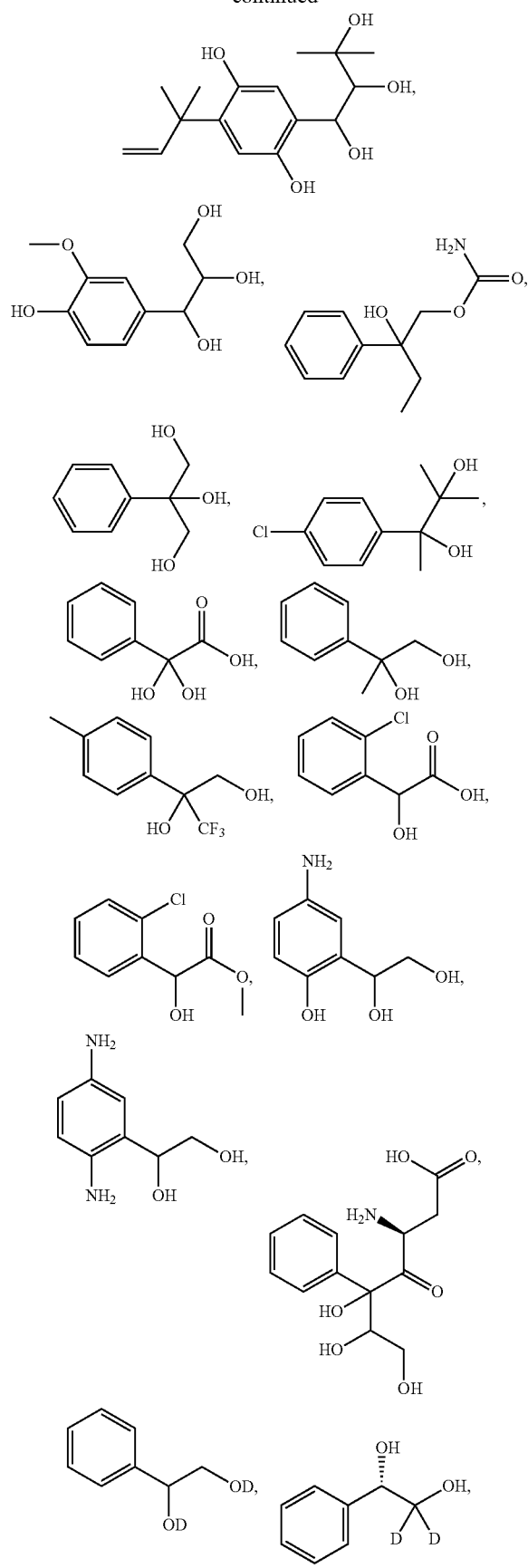
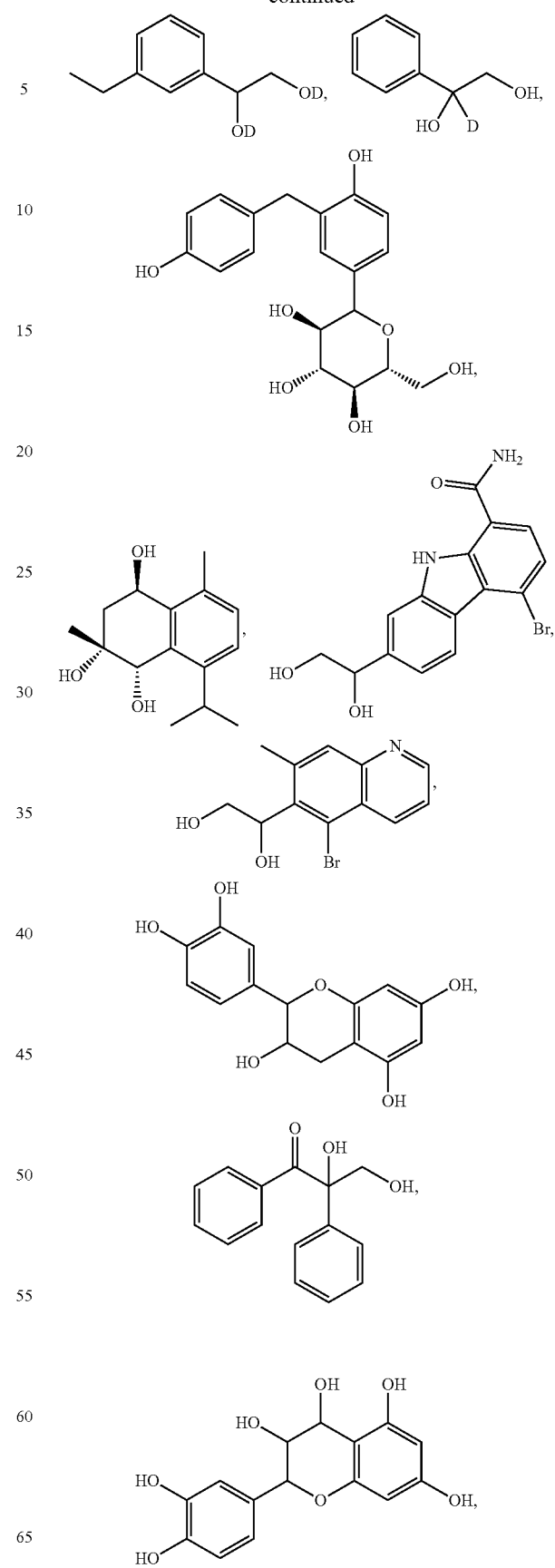

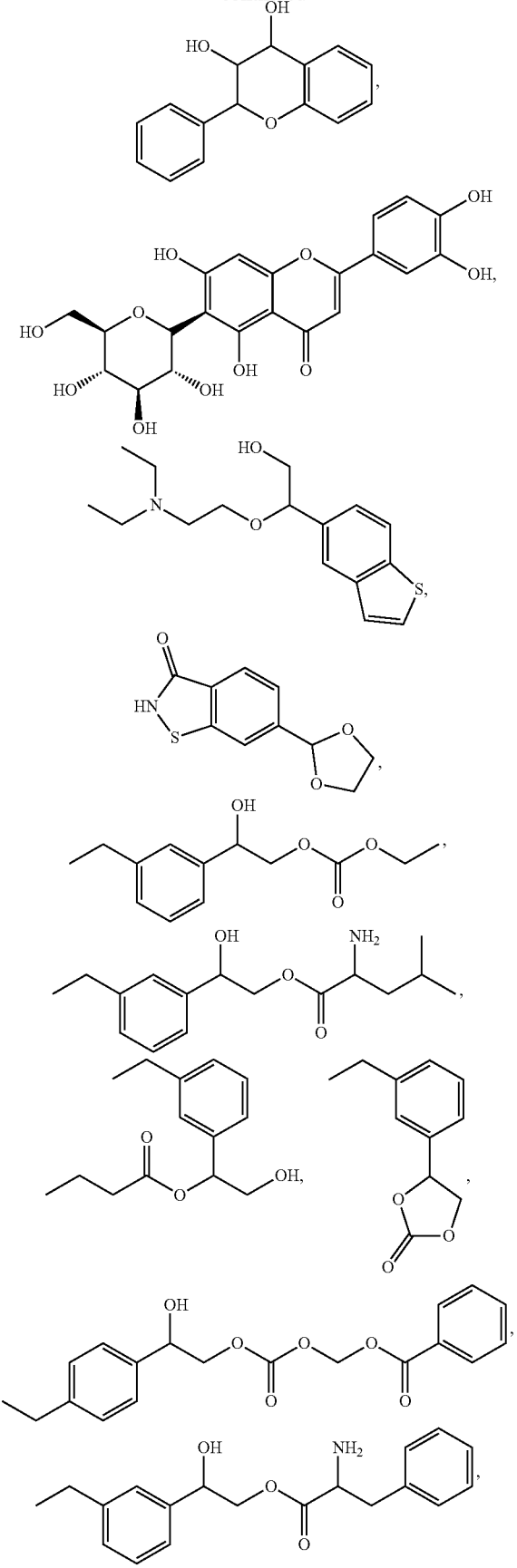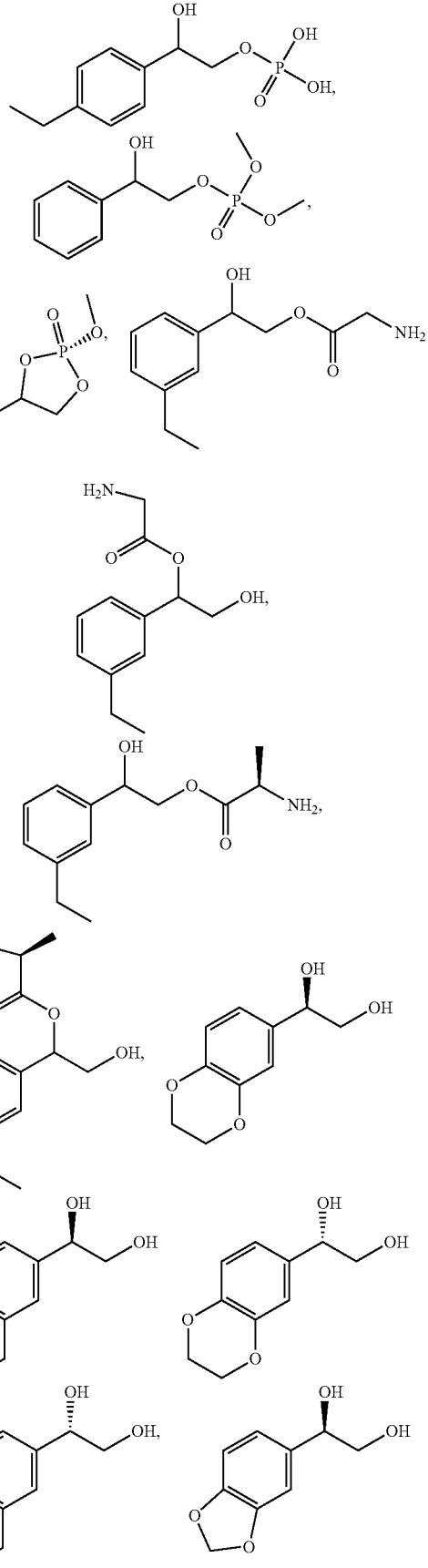

-continued

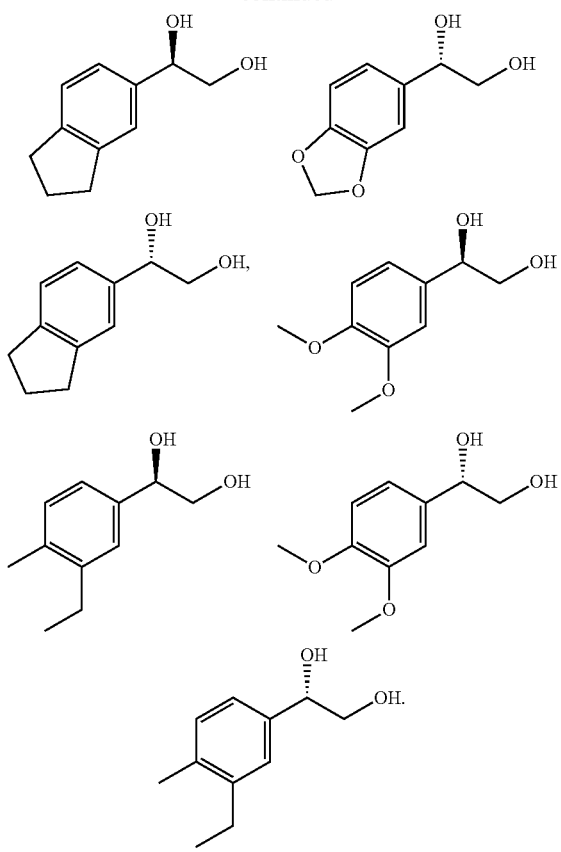

In a specific embodiment, the compound is

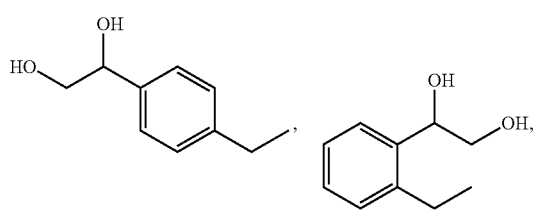

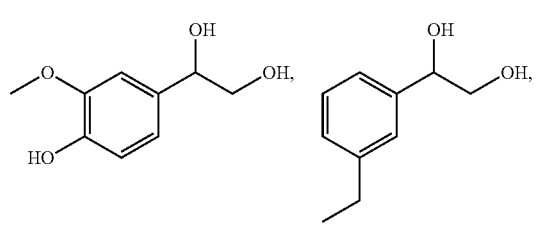

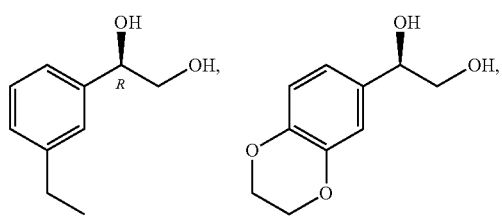

-continued

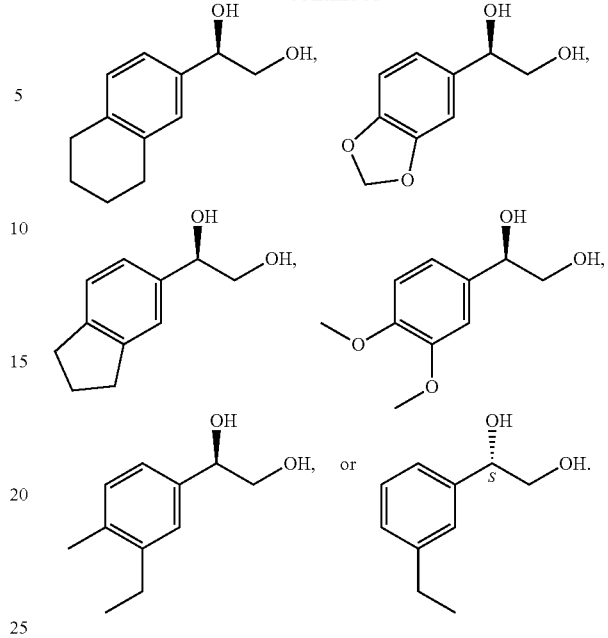

In particular embodiments, the hypertension-related diseases include, but are not limited to, cerebral apoplexy (cerebral hemorrhage and cerebral ischemia), hypertension heart disease, hypertension nephropathy, hypertension fundus lesions and retinal lesions, hypertension lower limb ischemia, and the like; The pulmonary hypertension-related diseases include, but are not limited to, idiopathic pulmonary hypertension, lung-derived heart disease, plateau heart disease, cardiovascular disease, pulmonary obstruction, fibrotic disorders, urinary system disorders.

In a second aspect, the present invention provides a compound of formula I, or a pharmaceutically acceptable salt or ester prodrug, optical isomer, stereoisomer or solvate thereof,

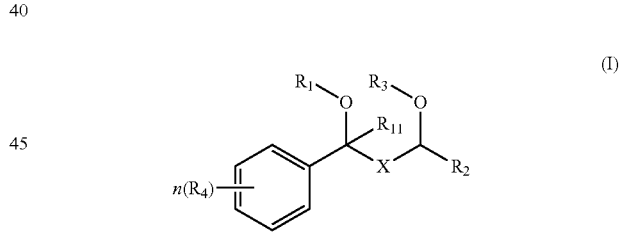

wherein,
X is absent or a substituted or unsubstituted C1-C3 linear or branched alkyl;
n is an integer of 0-5, preferably an integer of 1-5;
$R_1$ and $R_3$ are each independently selected from H, D, a substituted or unsubstituted C1-C10 alkyl, substituted or unsubstituted —$(CH_2CH_2O)_m$H, substituted or unsubstituted benzyl, substituted or unsubstituted phenyl, substituted or unsubstituted C1-C5 alkyl formyl, substituted or unsubstituted benzoyl, substituted or unsubstituted ester group, substituted or unsubstituted

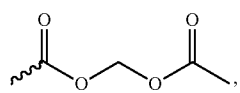

substituted or unsubstituted

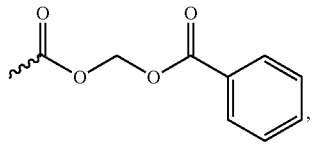

substituted or unsubstituted aminoacetyl, substituted or unsubstituted monosaccharide, disaccharide or polysaccharide group or substituted or unsubstituted phosphate group, where m is an integer of 0-5, preferably 0-3, most preferably 1-2; or $R_1$ and $R_3$ can form a five-membered ring

where $R_6$ is a substituted or unsubstituted C1-C5 alkyl;

$R_2$ and $R_{11}$ are each independently selected from H, D, a carbonyl, substituted or unsubstituted C1-C10 alkyl, substituted or unsubstituted phenyl, $CH_2OR_7$; $R_7$ is selected from H, a substituted or unsubstituted C1-C10 alkyl, substituted or unsubstituted monosaccharide, disaccharide or polysaccharide group;

$R_4$ is selected from H, D, a substituted or unsubstituted C1-C10 linear or branched alkyl, substituted or unsubstituted C1-C10 unsaturated linear or branched alkyl, hydroxyl, substituted or unsubstituted C1-C10 alkoxy, halogen, substituted or unsubstituted benzyl, substituted or unsubstituted phenyl, substituted or unsubstituted C1-C5 alkylformyl, substituted or unsubstituted benzoyl, nitro, COOH, substituted or unsubstituted C1-C5 alkoxyformyl, amino, substituted or unsubstituted C1-C5 alkylamino, substituted or unsubstituted C1-C5 alkylcarboxamido, substituted or unsubstituted benzoylamino, substituted or unsubstituted benzo-aromatic ring or five-membered or six-membered heterocyclic ring containing heteroatoms.

In a preferred embodiment, the phosphate group is as shown in

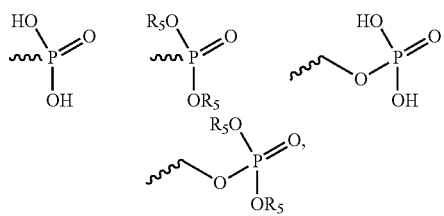

wherein $R_5$ is selected from a substituted or unsubstituted C1-C10 alkyl.

In a preferred embodiment, the substituted or unsubstituted aminoacetyl is as shown in

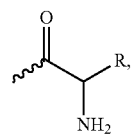

wherein R is various amino acid substituents.

In a preferred embodiment, the compound is used to prepare a medicament for preventing or treating hypertension or pulmonary hypertension.

In a specific embodiment, the compound is shown in Formula II,

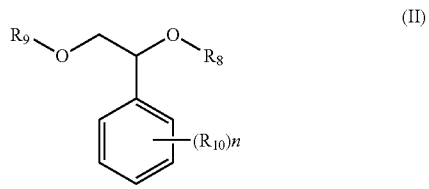

wherein, $R_5$ is selected from H, a substituted or unsubstituted C1-C10 alkyl, substituted or unsubstituted benzyl, substituted or unsubstituted C1-C5 alkylformyl, substituted or unsubstituted benzoyl, substituted or unsubstituted aminoacetyl, or substituted or unsubstituted monosaccharide, disaccharide or polysaccharide group;

$R_9$ is selected from H, a substituted or unsubstituted C1-C10 alkyl, substituted or unsubstituted benzyl, substituted or unsubstituted C1-C5 alkylformyl, substituted or unsubstituted benzoyl, substituted or unsubstituted aminoacetyl, or substituted or unsubstituted monosaccharide, disaccharide or polysaccharide group;

$R_{10}$ is selected from H, a substituted or unsubstituted C1-C10 linear or branched alkyl, substituted or unsubstituted C1-C10 unsaturated linear or branched alkyl, F, Cl, Br, hydroxyl, C1-C3 linear or branched alkoxy, substituted or unsubstituted C1-C5 alkyl formyl, substituted or unsubstituted benzoyl, or substituted or unsubstituted benzo-aromatic ring or five-membered or six-membered heterocyclic ring containing heteroatom (s); and n is any integer selected from 0-3.

In a specific embodiment, the compound is selected from following compounds, or a salt or ester, prodrug, optical isomer or solvate thereof:

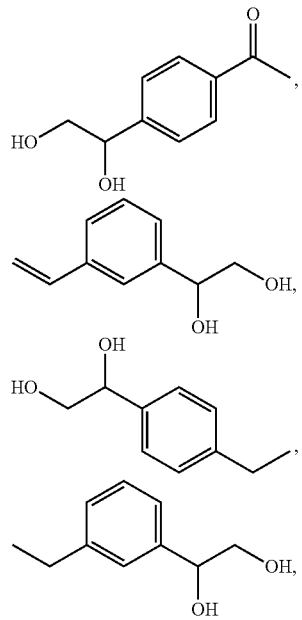

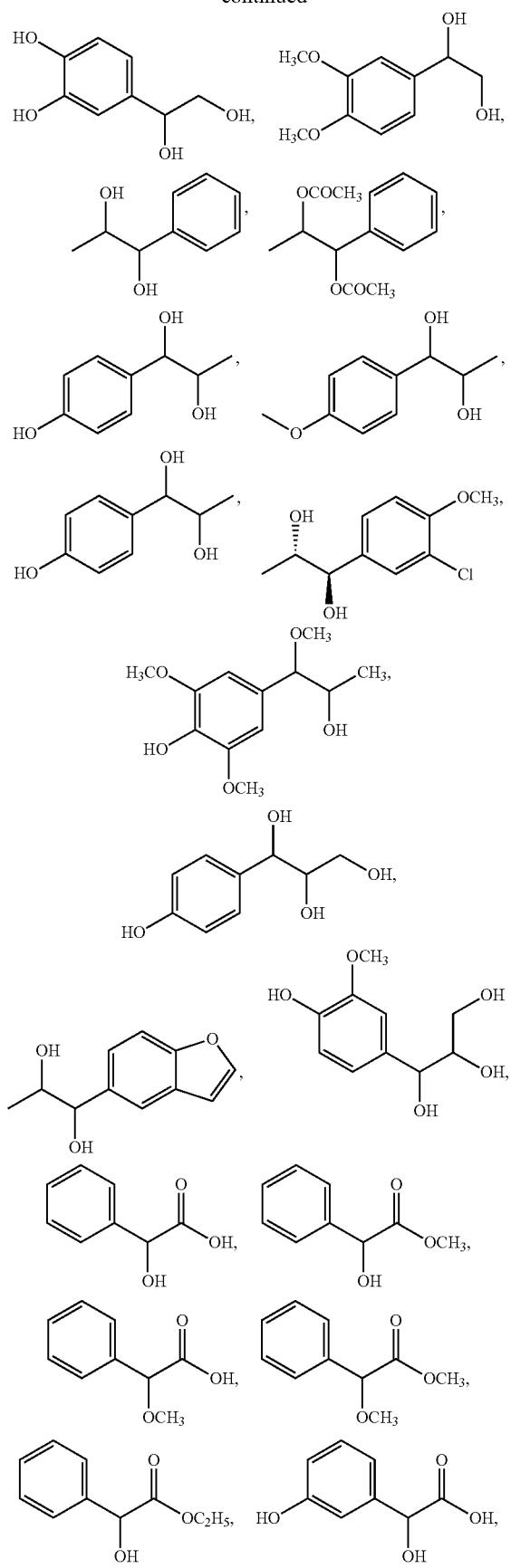
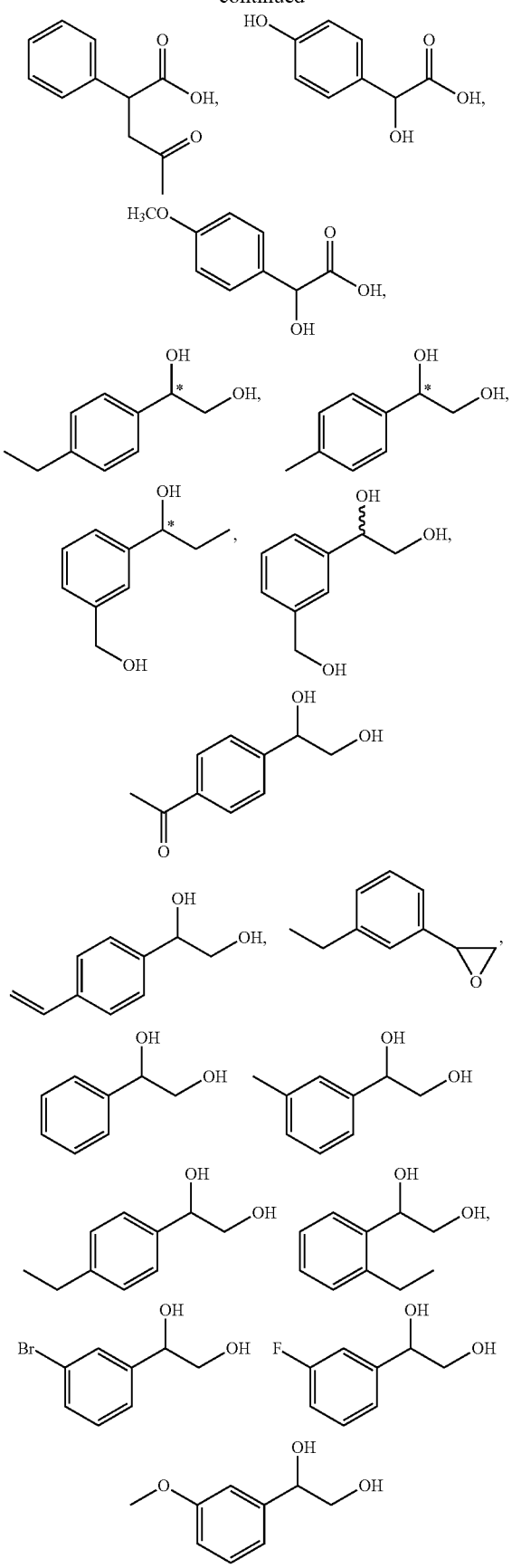

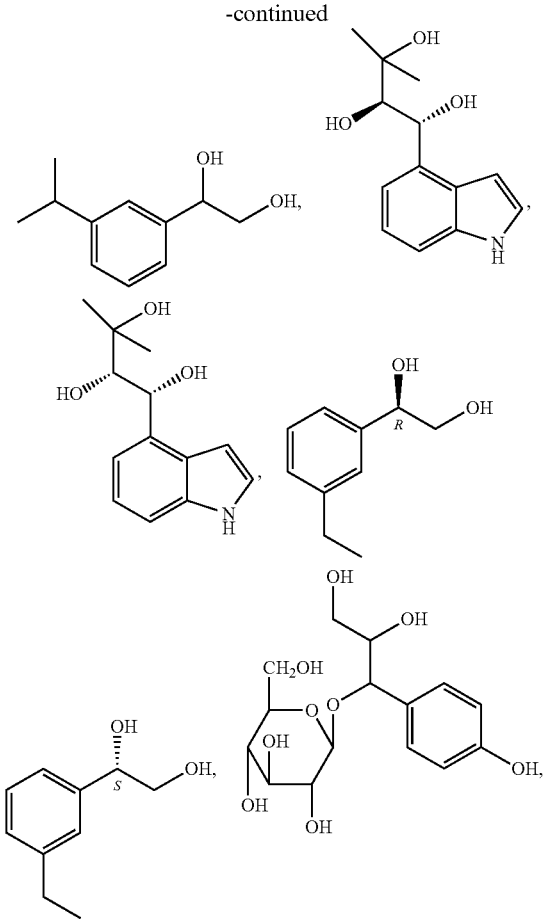
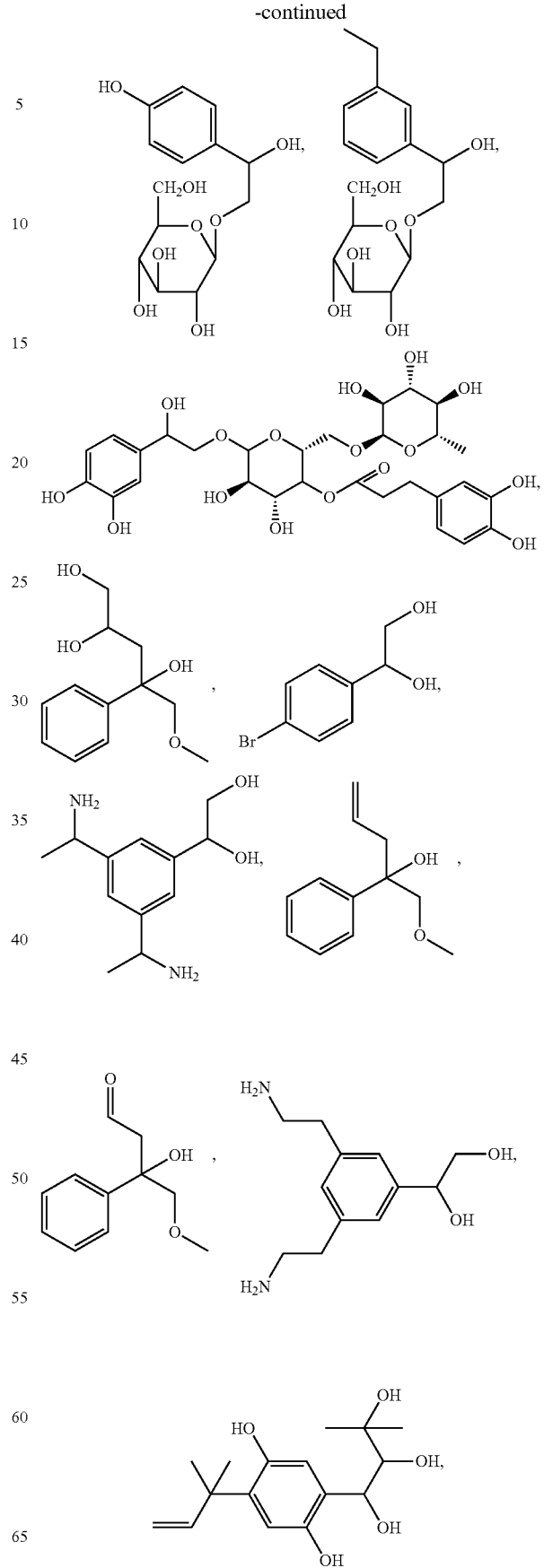

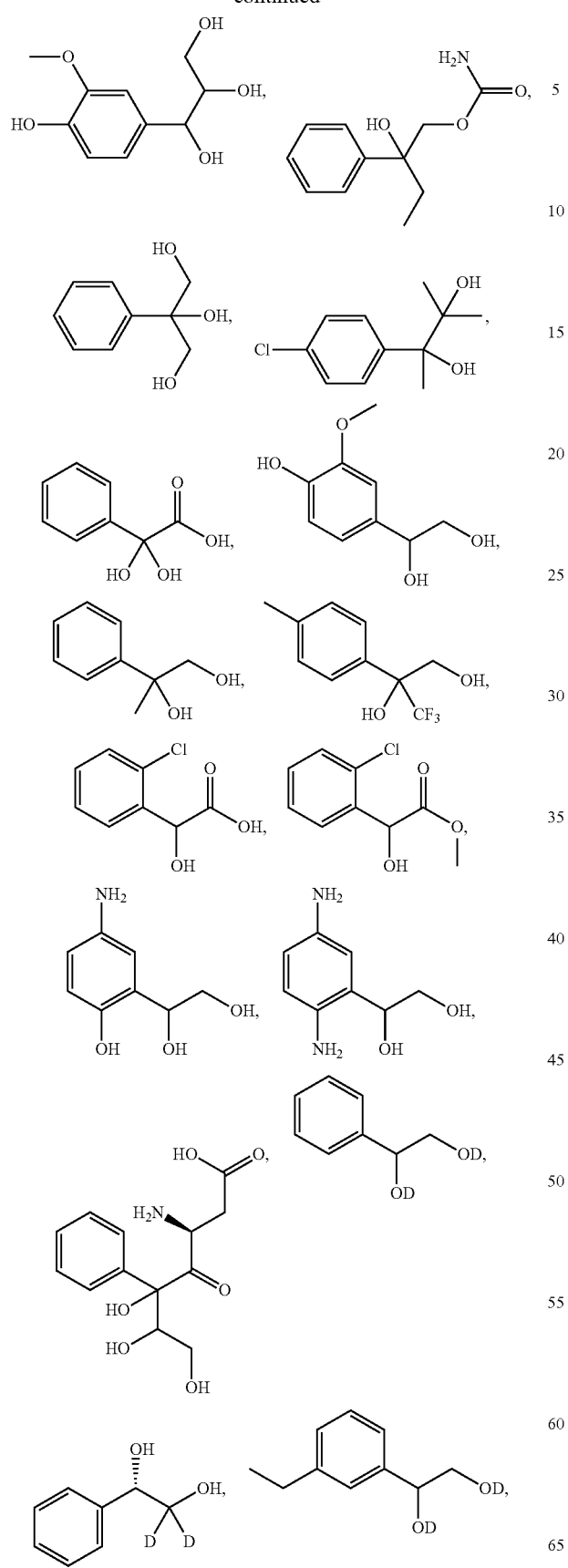
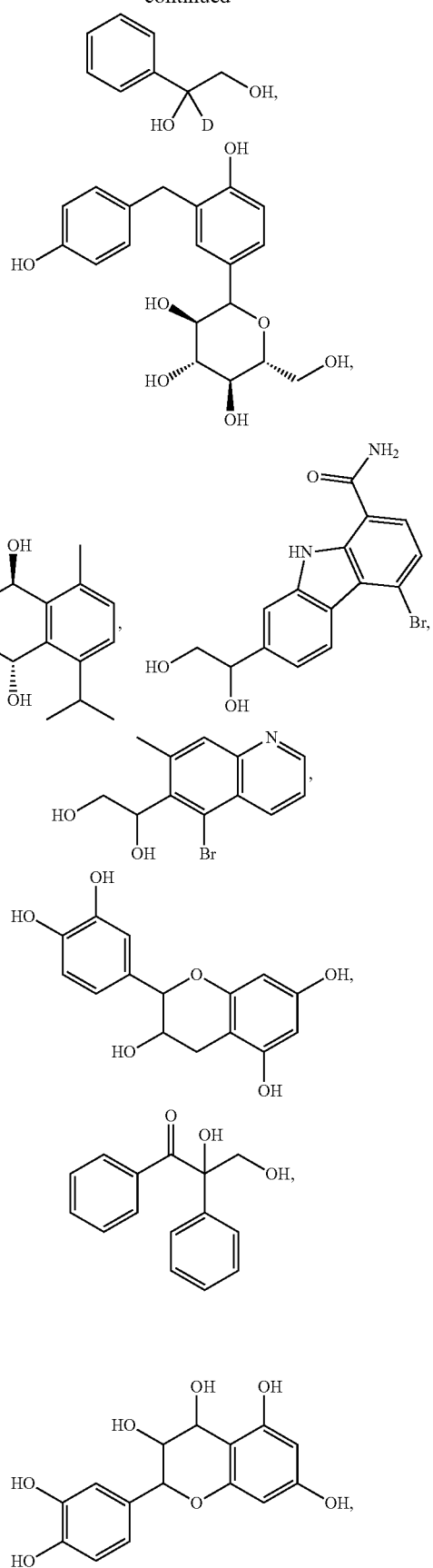

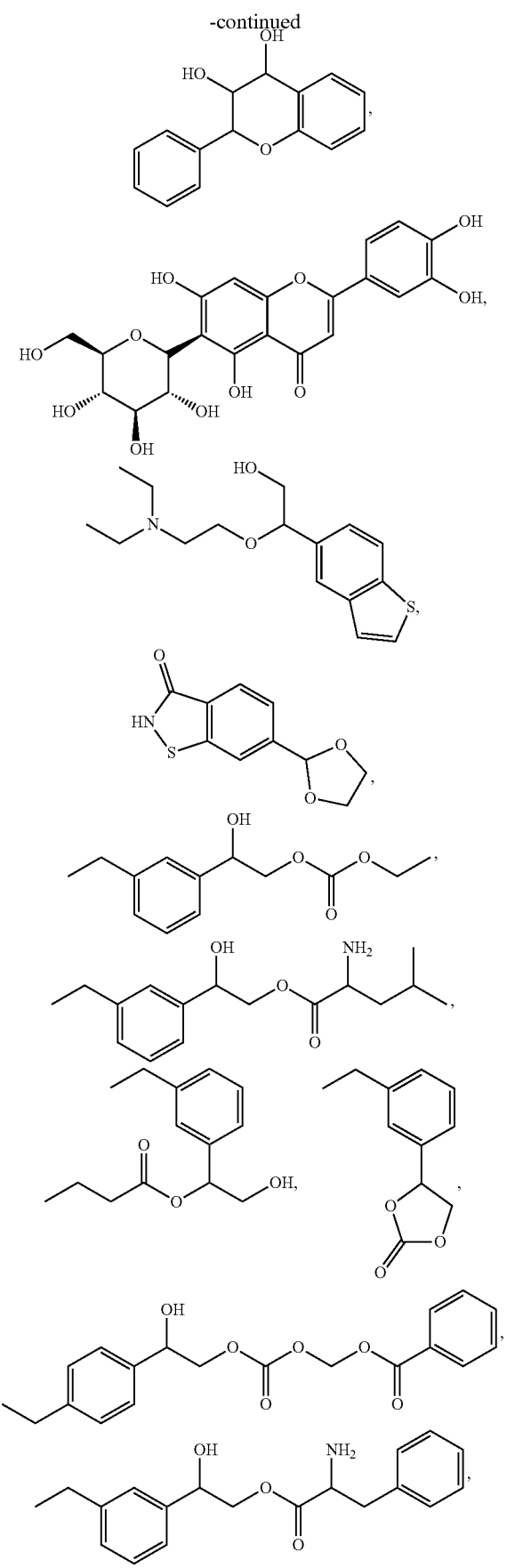
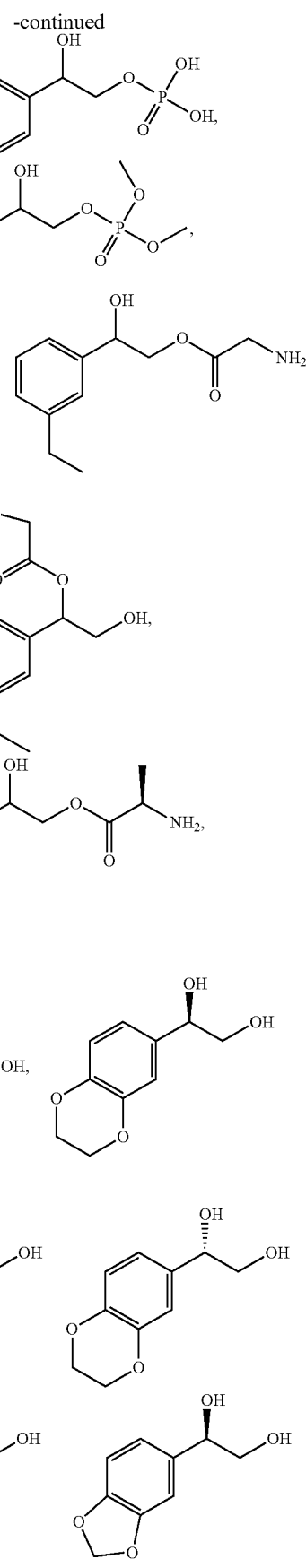

-continued

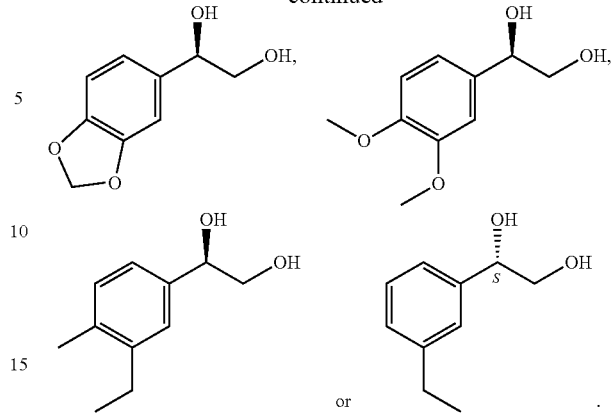

In a preferred embodiment, the compound is

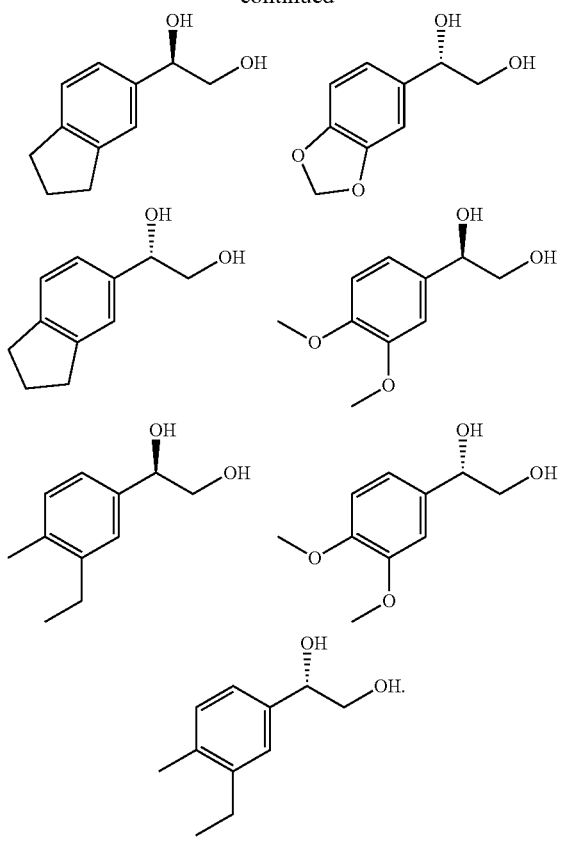

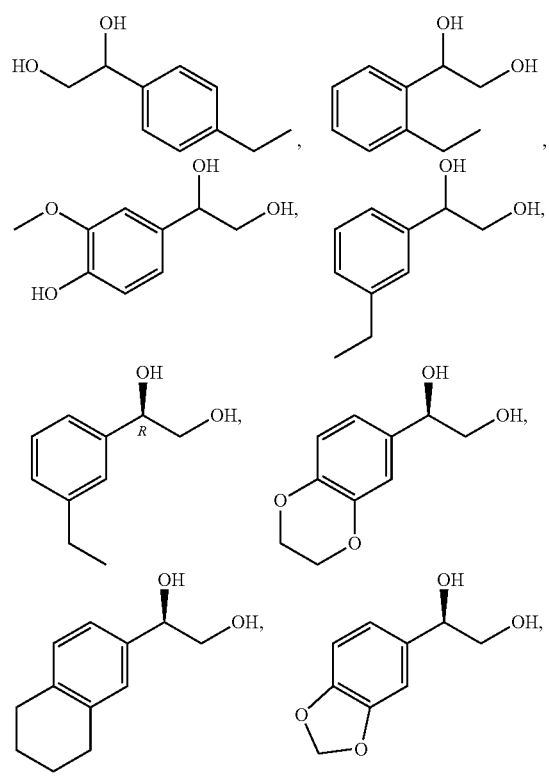

In a preferred embodiment, the compound is used in the preparation of a medicament for preventing or treating hypertension or hypertension-related diseases or pulmonary hypertension or pulmonary hypertension-related diseases, or is used to prevent or treat hypertension or hypertension-related diseases or pulmonary hypertension or pulmonary hypertension related diseases.

In a preferred embodiment, the hypertension-related diseases include, but are not limited to, cerebral apoplexy (cerebral hemorrhage and cerebral ischemia), hypertension heart disease, hypertension nephropathy, hypertension fundus lesions and retinal lesions, hypertension lower limb ischemia, and the like;

The pulmonary hypertension-related diseases include, but are not limited to, idiopathic pulmonary hypertension, lung-derived heart disease, plateau heart disease, cardiovascular disease, pulmonary obstruction, fibrotic disorders, urinary system disorders.

In a third aspect, the present invention provides a pharmaceutical composition comprising the compound of the second aspect, or a pharmaceutically acceptable salt or ester, prodrug, optical isomer, stereoisomer or solvate thereof, and a pharmaceutically acceptable carrier or excipient.

In a preferred embodiment, the pharmaceutical composition is used to prepare a medicament for preventing or treating hypertension or hypertension related diseases or pulmonary hypertension or pulmonary hypertension related diseases, or is used to prevent or treat of hypertension or hypertension related diseases or pulmonary hypertension or pulmonary hypertension related diseases.

In a preferred embodiment, the hypertension-related diseases include, but are not limited to, cerebral apoplexy (cerebral hemorrhage and cerebral ischemia), hypertension heart disease, hypertension nephropathy, hypertension fundus lesions and retinal lesions, hypertension lower limb ischemia, and the like;

The pulmonary hypertension-related diseases include, but are not limited to, idiopathic pulmonary hypertension, lung-derived heart disease, plateau heart disease, cardiovascular disease, pulmonary obstruction, fibrotic disorders, urinary system disorders.

In particular embodiments, the pharmaceutical composition is in a form for aerosolized inhalation.

In a fourth aspect, the present invention provides a method for preventing or treating hypertension or hypertension-related diseases or pulmonary hypertension or pulmonary hypertension related diseases, comprising administering to a subject in need thereof a therapeutically effective amount of a compound of the second aspect, or a pharmaceutically acceptable salt or ester, prodrug, optical isomer, stereoisomer or solvate thereof, or the pharmaceutical composition of the third aspect.

It is to be understood that the above-described technical features of the present invention and the various technical features described in detail below (eg, embodiments) may be combined with each other within the scope of the present invention to form a new or preferred technical solution, which will not be repeated herein:

MODES FOR CARRYING OUT THE INVENTION

Figure 1:
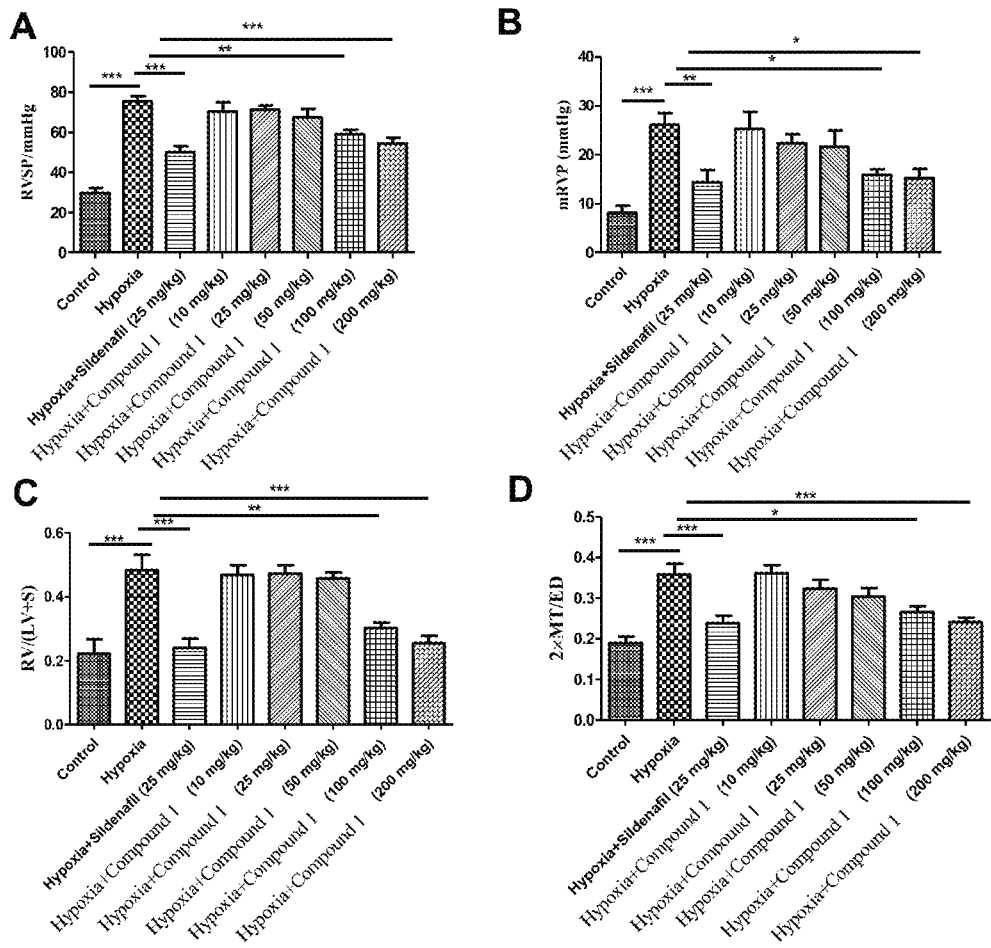
FIG. 1 shows therapeutic effects of orally administered compound 1 on low-oxygen pulmonary hypertension animal model.

The inventors have unexpectedly discovered a series of new compounds with therapeutic effects on hypertension and pulmonary hypertension. The mechanism of these compounds are different from existing therapeutic drugs, thereby establishing a brand new basis for the development of hypertension and pulmonary hypertension therapeutic drugs. Based on the above findings, the present invention is completed.

Terms

As used herein, the terms reagrding compounds, substituents, or structures have the same meaning as understood by a skilled person in the art. For clarity, the terms used herein are defined as follows.

As used herein, "a" or "an" includes the plural forms of the modified object, i.e., "a" or "an" refers to "at least one" or "one/more".

As used herein, expressions such as "$C_{1-n}$" refer to a group having 1-n carbon atoms, for example, the expression of "$C_{1-10}$" refers to a group having 1, 2, 3, 4, 5, 6, 7, 8, 9 or 10 carbon atoms; likewise, "C6-C10" refers to a group having 6, 7, 8, 9 or 10 carbon atoms.

As used herein, the term "alkyl" has the same meaning as commonly understood by a skilled person in the art and refers to a variety of saturated or unsaturated linear, pendant or cyclic hydrocarbon radicals. For example, an alkyl described herein refer to lower an alkyl of 1 to 10 carbon atoms; preferably, a lower alkyl of 1 to 8 carbon atoms; more preferably, a lower alkyl of 1 to 6 carbon atoms. In a particular embodiment, the alkyl described herein includes, but are not limited to, methyl, ethyl, propyl, isopropyl, butyl, isobutyl, sec-butyl, tert-butyl, pentyl, hexyl, heptyl, etc.

As used herein, the term "aryl" has the same meaning as commonly understood by a skilled person in the art and refers to a cyclic conjugated aromatic system. For example, the term "C6-C10 aryl" refers to an aromatic ring group having 6 to 10 carbon atoms while not containing a heteroatom in the ring, such as phenyl, naphthyl, and the like. As used herein, the term "heteroaryl" refers to a cyclic conjugated aromatic system, in which one or more heteroatoms such as N, O or S are contained; for example, pyridyl and pyrazinyl.

As used herein, the term "aminoacetyl" has a conventional meaning as understood by a skilled person in the art, i.e., an amino-substituted acetyl. In a particular embodiment, the aminoacetyl is shown in

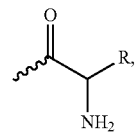

wherein R is a variety of amino acid substituents.

As used herein, the term "heterocyclyl" refers to a saturated or partially unsaturated, non-aromatic cyclic group comprising a monocyclic, fused, spiro or bridged ring, wherein the heterocyclic ring has at least one heteroatom selected from O, S or N as a ring member. For example, "5 or 6 membered heterocyclyl" refers to a saturated or unsaturated 5 or 6 membered cycloalkyl having from 1 to 3 heteroatoms selected from oxygen, sulfur or nitrogen on a ring, such as dioxolyl, etc.

As used herein, the term "halogen" refers to F, Cl, Br, or I.

Based on the teachings of the present invention and common knowledge in the art, a skilled person will understand that the compounds of the present invention, as well as the various substituents defined above, may be further substituted, such as substituted with a C1-6 alkyl, C1-6 alkoxy, halogen, nitro, amino, phenyl, hydroxyl, etc, as long as the combination of the desired substituents is stable or a chemically achievable substituent combination.

As used herein, the term "substituted" means that one or more hydrogen atoms on a particular group are replaced by particular substituents. A particular substituent may be a substituent previously described herein, or may be a particular substituent present in various embodiments. Therefore, in the present invention, the substituent in the general formula (I) or (II) can each independently be a corresponding group in a specific compound in an embodiment; that is, the present invention includes a combination of each substituent in the general formula (I) or (II) described above, and also includes a combination of a part of substituents shown in the general formula (I) or (II) and other specific substituents present in the embodiment.

Unless specifically stated, a substituted group may have a particular substituent at any substitutable site of the group, which may be the same or different in various sites. A cyclic substituent, such as a heterocyclyl, may be bound to another ring, such as cycloalkyl, to form a spirobicyclic ring system, for example, two rings having a common carbon atom. Such substituent is, for example but not limited to, a $C_{1-8}$ alkyl, $C_{2-8}$ alkenyl, $C_{2-8}$ alkynyl, $C_{3-8}$ cycloalkyl, 3- to 12-membered heterocyclyl, aryl, heteroaryl, halogen, hydroxy, carboxyl (—COOH), $C_{1-8}$ aldehyde group, $C_{2-10}$ acyl, $C_{2-10}$ ester group, amino, $C_{1-8}$ alkoxy, nitro, cyano, mercapto, amino, and the like.

In a particular embodiment, a hydrogen atom on an alkyl and aryl is substituted with amino, halogen, or other groups, thereby becoming the group belonging to each of the above definitions.

For convenience and in compliance with the conventional understanding in the art, the terms "optionally", "optionally substituted" or "substituted or unsubstituted" are only applicable to sites that can be substituted with substituents, and do not include those that are chemically unachievable.

Compounds of the Invention

The present invention provides a series of brand-new compounds having therapeutic effects on hypertension and pulmonary hypertension having different mechanisms than existing therapeutic drugs.

In a particular embodiment, the present invention provides a compound of Formula I or II, or a pharmaceutically acceptable salt or ester, prodrug, optical isomer, stereoisomer or solvate thereof,

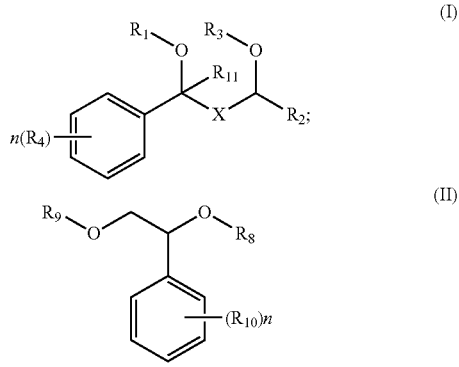

Substituents in the general formula are described as said above.

The compounds of the present invention can be prepared into a pharmaceutically acceptable salt or ester, prodrug, optical isomer, stereoisomer, or solvate by a skilled person. For example, the compounds of the present invention may be reacted with an inorganic or organic acid to form conventional pharmaceutically acceptable salts. The inorganic acid includes hydrochloric acid, hydrobromic acid, sulfuric acid, nitric acid, aminosulfonic acid, phosphoric acid, etc., and the organic acid includes various amino acids, citric acid, tartaric acid, lactic acid, pyruvic acid, acetic acid, benzenesulfonic acid, p-toluenesulfonic acid, methanesulfonic acid, naphthalenesulfonic acid, ethanesulfonic acid, naphthalenedisulfonic acid, maleic acid, malic acid, malonic acid, fumaric acid, succinic acid, propionic acid, oxalic acid, trifluoroacetic acid, stearic acid, hexanoic acid, hydroxymaleic acid, phenylacetic acid, benzoic acid, salicylic acid, glutamic acid, ascorbic acid, p-aminobenzenesulfonic acid, 2-acetoxybenzoic acid and isethionic acid, and the like; or the compound of the invention forms sodium, potassium, calcium, aluminum or ammonium salts with an inorganic base; or forms methylamine, ethylamine or ethanolamine salts with an organic base.

Due to the presence of chiral carbon atoms in the compounds of the present invention, the optical isomers or stereoisomers obtained by resolving the compounds of the present invention also fall within the scope of the present invention.

Based on the compound of the present invention or a pharmaceutically acceptable salt or ester, prodrug, optical isomer, stereoisomer, or solvate thereof, a pharmaceutical composition comprising a compound of the invention and optionally a pharmaceutically acceptable excipient is also provided in the present invention.

In a particular embodiment, the pharmaceutical composition of the present invention comprises a compound of the invention or a pharmaceutically acceptable salt thereof and a pharmaceutically acceptable excipient or carrier within a safe and effective amount. "Safe effective amount" means that the amount of the compound is sufficient to significantly improve the condition without creating severe side effects.

A "pharmaceutically acceptable excipient or carrier" refers to one or more compatible solid or liquid fillers or gels that are suitable for humans and must have sufficient purity and sufficiently low toxicity. As used herein, "compatibility" meants that the components of the composition and the compound of the present invention can be intermingled with each other without significantly reducing the efficacy of the compound. Examples of the pharmaceutically acceptable carrier are cellulose and derivatives thereof (e.g., sodium carboxymethylcellulose, sodium ethylcellulose, cellulose acetate, etc.), gelatin, talc, solid lubricants (e.g., stearic acid, magnesium stearate), calcium sulfate, vegetable oils (e.g., soybean oil, sesame oil, peanut oil, olive oil, etc.), polyols (e.g., propylene glycol, glycerol, mannitol, sorbitol, etc.), emulsifiers (e.g., Tween®), wetting agents (e.g., sodium dodecyl sulfate), colorants, flavoring agents, stabilizers, antioxidants, preservatives, pyrogen-free raw water, etc.

The administration of the compound or pharmaceutical composition of the present invention is not particularly limited, and representative administration modes include, but are not limited to: oral, intratumoral, rectal, parenteral (intravenous, intramuscular, or subcutaneous), and topical administration.

Solid dosage forms for oral administration include capsules, tablets, pills, powders, and granules. In these solid dosage forms, the active compound is combined with at least one conventional inert excipient (or carrier), such as sodium citrate or dicalcium phosphate, or with following ingredients: (a) fillers or compatibilizers such as starch, lactose, sucrose, glucose, mannitol, and silicic acid; (b) adhesives such as hydroxymethyl cellulose, alginate, gelatin, polyvinyl pyrrolidone, sucrose, and arabic gum; (c) humectants such as glycerol; (d) disintegrants such as agar, calcium carbonate, potato starch or tapioca starch, alginic acid, certain complex silicates, and sodium carbonate; (e) retarding solvent such as paraffin; (f) absorbent accelerators, e.g., quaternary amine compounds. (g) wetting agents such as cetyl alcohol and glycerol monostearate; (h) adsorbents, e.g., kaolin; and (i) lubricants such as talc, calcium stearate, magnesium stearate, solid polyethylene glycol, sodium lauryl sulfate, or a mixture thereof. For capsules, tablets, and pills, the dosage form may also comprise a buffer.

Solid dosage forms, such as tablets, pills, capsules, pills, and granules may be prepared using a coating and a shell material, such as casings and other materials known in the art. They may comprise opacifying agents, and the active compounds or compounds in such compositions may be released in some portion of the digestive tract in a delayed manner. Examples of useful embedding components are polymeric and wax-based materials. The active compound may also form a microcapsule form with one or more of the excipients described above, if necessary.

Liquid dosage forms for oral administration include pharmaceutically acceptable emulsions, solutions, suspensions, syrups or tinctures. In addition to the active compounds, liquid dosage forms may include inert diluents conventionally employed in the art, such as water or other solvents, solubilizers and emulsifiers, such as ethanol, isopropyl alcohol, ethyl carbonate, ethyl acetate, propylene glycol, 1,3-butanediol, dimethylformamide and oils, especially cottonseed oil, peanut oil, corn germ oil, olive oil, castor oil and sesame oil or mixtures thereof, etc.

In addition to these inert diluents, the composition may also include adjuvants such as wetting agents, emulsifiers and suspending agents, sweeteners, flavoring agents, and fragrances.

In addition to the active compound, the suspension may comprise suspending agents such as ethoxylated isostearyl alcohol, polyoxyethylene sorbitol and sorbitan esters, microcrystalline cellulose, methanol aluminum and agar or mixtures thereof, etc.

Compositions for parenteral injection may include physiologically acceptable sterile aqueous or non-aqueous solutions, dispersions, suspensions or emulsions, and sterile powders for redissolving into sterile injectable solutions or dispersions. Suitable aqueous and non-aqueous carriers, diluents, solvents, or excipients include water, ethanol, polyols, and suitable mixtures thereof.

Dosage forms of the compound of the invention for topical administration include ointments, powders, patches, sprays, and inhalants. The active ingredient is mixed with a physiologically acceptable carrier and any preservative, buffer, or propellant (if necessary) under sterile conditions.

The compounds of the present invention may be administered alone or in combination with other pharmaceutically acceptable compounds. When a pharmaceutical composition is used, a safe and effective amount of the compound of the present invention is used for a mammal (e.g., a human) in need of the treatment, wherein the administered dosage is a pharmaceutically effective amount. The compound and pharmaceutical composition of the present invention can be administered through oral, nasal, skin, lung, or gastrointestinal administration routes, preferably oral, in one-time administration or divided administration. Regardless of the method of administration, the optimal dosage for an individual should be determined based on the specific treatment. Usually the dosage is gradually increased from a small dosage until the suitable dosage is found. Factors, such as the route of administration, the health of a patient status, and the like shall be considered for the specific dosage, which are within the skill of a skilled person. In a particular embodiment, the compound of the present invention is preferably in a form suitable for nebulized administration.

Advantages of the Invention

1. The present invention provides a series of new compounds having therapeutic effects on hypertension and pulmonary hypertension; and
2. The mechanisms of the compounds of the present invention for treating hypertension and pulmonary hypertension are different from existing drugs, thereby potentially developing new therapeutic drugs for hypertension and pulmonary hypertension.

The technical solution of the present invention will be further described below in conjunction with specific implementation cases, but the following implementation cases do not constitute a limitation to the present invention. All various application methods adopted in accordance with the principles and technical means of the present invention belong to the scope of the present invention. The experimental methods that do not indicate specific conditions in the following examples usually follow the conventional conditions or the conditions recommended by the manufacturer. Unless otherwise stated, percentages and parts are calculated by weight.

EXAMPLES

Preparation Method for the Compounds

The compounds of the present invention may be prepared according to conventional routes or methods and may also be obtained in accordance with the methods or routes described herein.

Synthesis

Example 1. Synthesis of Compound 1

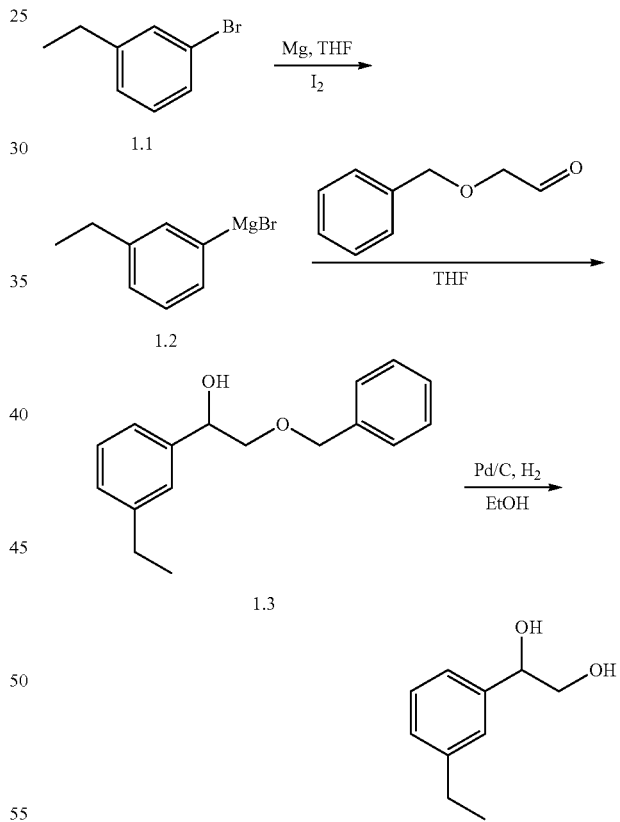

1. Synthesis of Compound 1.3

Magnesium powders (2.2 g, 90 mmol) were placed in a 250 mL three-mouth reaction flask, a grain of iodine was added, the compound 1.1 (15 g, 82 mmol) was dissolved in 120 mL of anhydrous tetrahydrofuran, and 10 mL of the tetrahydrofuran solution of Compound 1 was added dropwise into the reaction flask containing magnesium powders via a constant pressure drop funnel. The reaction was initiated by using a hair dryer, and then the remaining 110 mL of the tetrahydrofuran solution of Compound 1.1 was slowly added dropwise after the reaction was started. Upon addition, the reaction was refluxed for 3.5 hours, and the tetrahydrofuran solution of compound 1.2 was finally obtained.

In an ice bath, the tetrahydrofuran solution of Compound 1.2 was added dropwise to 80 mL of solution of benzyloxyacetaldehyde (12 g, 80 mmol) in anhydrous tetrahydrofuran. Upon addition, the solution was raised to room temperature for 1 hour and then a saturated aqueous solution of ammonium chloride was added to quench the reaction. Finally, tetrahydrofuran was removed and the resulted solution was extracted with ethyl acetate, dried over anhydrous sodium sulfate, and purified by column (PE:EA=10:1) to yield 12.4 g of target compound with a two-step yield of 59.6%. $^1$H NMR (400 MHz, DMSO): δ 7.36-7.15 (m, 8H), 7.09 (d, J=7.6 Hz, 1H), 5.38 (d, J=4.4 Hz, 1H), 4.74-4.70 (m, 1H), 4.51 (s, 2H), 3.53-3.44 (m, 2H), 2.61 (q, J=7.6, 2 H), 1.19 (t, J=7.6, 3H). LC-MS: 255.30 (M−H)$^-$.

2. Synthesis of Compound 1

Compound 1.3 (12.4 g, 48.4 mmol) was dissolved in 70 mL of ethanol, 10% palladium carbon (2.43 g) was added, air was replaced with $H_2$, and the reaction system was stirred for 3 hours at 38° C. After the reaction was completed, the solvent was removed and the residue was purified through a column (PE:EA=5:1) to afford 6.42 g of the target compound with a yield of 79%. $^1$H NMR (400 MHz, CDCl$_3$): δ 7.28-7.12 (m, 4H), 4.78 (dd, J$_1$=8.0 Hz, J$_2$=3.6 Hz, 1H), 3.74-3.62 (m, 2H), 2.64 (q, J=7.6 Hz, 2H), 1.23 (t, J=7.6 Hz, 3H). LC-MS: 165.10 (M−H)$^-$.

Example 2. Synthesis of Compound 2

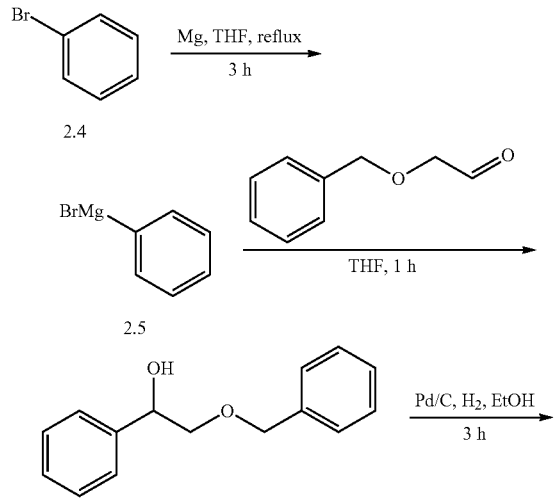

1. Synthesis of Compound 2.6

Magnesium powders (0.17 g, 7 mmol) were placed in a 50 mL three-mouth reaction flask, a grain of iodine was added, compound 2.4 (1 g, 6.4 mmol) was dissolved in anhydrous tetrahydrofuran (12 mL), 2 mL of the solution of Compound 4 in tetrahydrofuran was added into the reaction flask dropwise by a constant-pressure drop funnel, the reaction was initiated with a hair dryer, and the remaining 10 mL of the solution of Compound 2.4 in tetrahydrofuran was slowly added dropwise after the reaction was initiated. Upon addition, the reaction was refluxed for 3.5 hours, and finally the solution of Compound 2.5 in tetrahydrofuran was obtained.

In an ice bath, a solution of Compound 2.5 in tetrahydrofuran was added dropwise to 8 mL of a solution of benzyloxyacetaldehyde (0.97 g, 6.4 mmol) in anhydrous tetrahydrofuran. Upon addition, the solution was raised to room temperature for 1 hour, and then a saturated aqueous solution of ammonium chloride was added to quench the reaction. Finally, tetrahydrofuran was removed and the obtained residue was extracted with ethyl acetate, dried over anhydrous sodium sulfate, purified through a column (PE:EA=10:1) to yield 0.98 g of the target compound with a two-step yield of 67.6%. $^1$H NMR (400 MHz, DMSO): δ 7.37-7.22 (m, 10H), 5.41 (d, J=4.0 Hz, 1H), 4.78-4.74 (m, 1H), 4.51 (s, 2H), 3.51-3.48 (m, 2H). LC-MS: 227.30 (M−H)$^-$.

2. Synthesis of Compound 2

Compound 2.6 (0.9 g, 4 mmol) was dissolved in ethanol (10 mL), 10% palladium carbon (0.2 g) was added, air was replaced with $H_2$, and the reaction was stirred for 3 hours at 38° C. After the reaction was completed, the solvent was removed and the obtained residue was purified through a column (PE:EA=5:1) to yield 0.24 g of target compound with a yield of 45%. $^1$H NMR (400 MHz, DMSO): δ 7.34-7.28 (m, 4H), 7.24-7.20 (m, 1H), 5.24 (d, J=4.4 Hz, 1H), 4.74 (t, J=6 Hz, 1H), 4.55 (q, J=6 Hz, 1H), 3.43 (t, J=6 Hz, 2H). LC-MS: 137.10 (M−H)$^-$.

Example 3. Synthesis of Compound 3

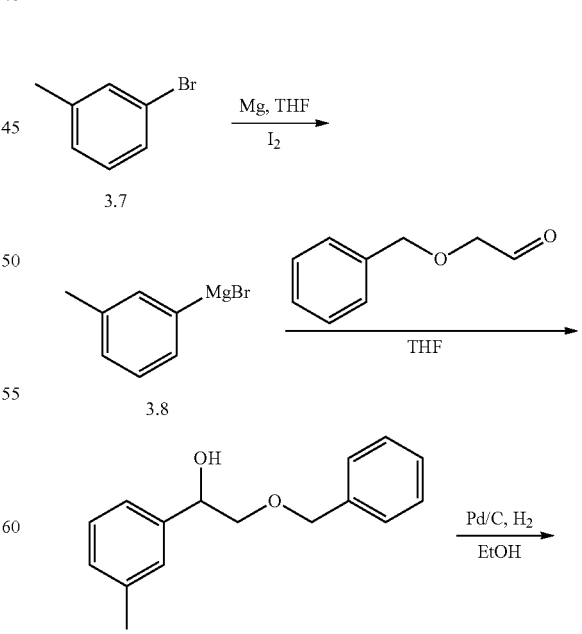

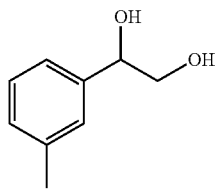

3

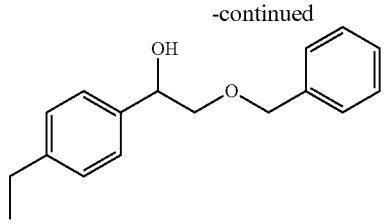

4.12

1. Synthesis of Compound 3.9

Magnesium powders (0.33 g, 13.8 mmol) were placed in a 100 mL three-mouth reaction flask, a grain of iodine was added, compound 3.7 (2 g, 11.7 mmol) was dissolved in anhydrous tetrahydrofuran (20 mL), the solution of compound 3.7 in tetrahydrofuran (3 mL) was added dropwise into a reaction bottle by a constant-pressure drop funnel, the reaction was initiated with an electric hair drier, and the remaining solution of Compound 7 in tetrahydrofuran (17 mL) was slowly added dropwise after the reaction was started. Upon addition, the reaction was refluxed for 3.5 hours, and finally a solution of compound 3.8 in tetrahydrofuran was obtained.

In an ice bath, the solution of compound 3.8 in tetrahydrofuran was added dropwise to a solution of benzyloxyacetaldehyde (1.74 g, 11.6 mmol) in anhydrous tetrahydrofuran (14 mL). Upob addition, the reaction was raised to room temperature for 1 hour, and then a saturated aqueous solution of ammonium chloride was added to quench the reaction. Finally, tetrahydrofuran was removed and the obtained residue was extracted with ethyl acetate, dried over anhydrous sodium sulfate, and purified by a column (PE:EA=10:1) to yield 0.95 g of target compound with a two-step yield of 34%. $^1$H NMR (400 MHz, DMSO): δ 7.34-7.04 (m, 9H), 5.34 (d, J=4.0 Hz, 1H), 4.73-4.69 (m, 1H), 4.51 (s, 2H), 3.52-3.43 (m, 2H), 2.28 (s, 3H). LC-MS: 241.30 (M−H)$^-$.

2. Synthesis of Compound 3

Compound 3.9 (0.9 g, 3.8 mmol) was dissolved in ethanol (10 mL) and 10% palladium carbon (0.2 g) was added, air was replaced with H$_2$, and the reaction system was stirred for 3 hours at 38° C. After the reaction was completed, the solvent was removed and purified by a column (PE:EA=5:1) to yield 0.28 g of target compound with a yield of 50%. $^1$H NMR (400 MHz, CDCl$_3$). δ 7.26-7.09 (m, 4H), 4.76 (dd, J$_1$=8.0 Hz, J$_2$=3.6 Hz, 1H), 3.72-3.59 (m, 2H), 3.09 (s, 2H), 2.34 (s, 3H). LC-MS: 151.10 (M−H)$^-$.

Example 4. Synthesis of Compound 4

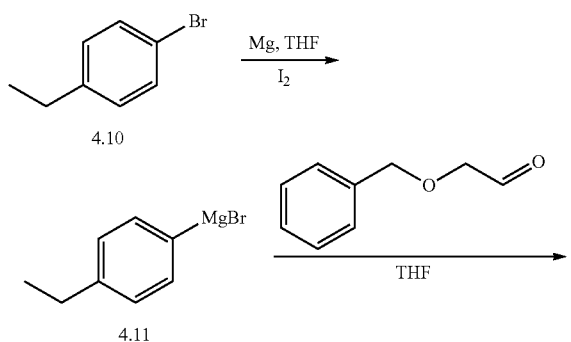

4

1. Synthesis of Compound 4.12

Magnesium powders (0.31 g, 12.9 mmol) were placed in a 100 mL three-mouth reaction flask, a grain of iodine was added, compound 4.10 (2 g, 10.9 mmol) was dissolved in anhydrous tetrahydrofuran (20 mL), the solution of compound in tetrahydrofuran (3 mL) was added dropwise into a reaction bottle by a constant-pressure drop funnel, and the reaction was initiated with an electric hair drier. The remaining 17 mL of the solution of compound 4.10 in tetrahydrofuran was slowly added dropwise after the reaction was started. Upon addition, the reaction was refluxed for 3.5 hours, and finally a solution of compound 11 in tetrahydrofuran was obtained.

In an ice bath, a solution of compound 4.11 in tetrahydrofuran was added dropwise to a solution of benzyloxyacetaldehyde (1.62 g, 10.8 mmol) in anhydrous tetrahydrofuran (14 mL). Upon addition, the reaction was raised to room temperature for 1 hour, and then a saturated aqueous solution of ammonium chloride was added to quench the reaction. Finally, tetrahydrofuran was removed and the obtained residue was extracted with ethyl acetate, dried over anhydrous sodium sulfate, purified by a column (PE:EA=10:1) to afford 1 g of the target compound with a two-step yield of 36%. $^1$H NMR (400 MHz, DMSO): δ 7.35-7.14 (m, 9H), 5.33 (d, J=4.0 Hz, 1H), 4.74-4.70 (m, 1H), 4.51 (s, 2H), 3.52-3.43 (m, 2H), 2.57 (q, J=7.6 Hz, 2H), 1.16 (t, J=7.6 Hz, 3H). LC-MS: 255.30 (M−H)$^-$.

2. Synthesis of Compound 4

Compound 4.12 (0.9 g, 3.5 mmol) was dissolved in ethanol (10 mL) and 10% palladium carbon (0.2 g) was added, air was replaced with H$_2$, and the reaction system was stirred for 3 hours at 38° C. After the reaction was completed, the solvent was removed and the obtained residue was purified by a column (PE:EA=5:1) to yield 0.24 g of target compound with a yield of 37%. $^1$H NMR (400 MHz, CDCl$_3$): δ 7.20-7.10 (m, 4H), 4.72 (dd, J$_1$=8.0 Hz, J$_2$=3.6 Hz, 1H), 3.66-3.55 (m, 2H), 2.59 (q, J=7.6 Hz, 2H), 2.46 (s, 2H), 1.15 (t, J=7.6 Hz, 3H). LC-MS: 165.10 (M−H)$^-$.

Example 5. Synthesis of Compound 5

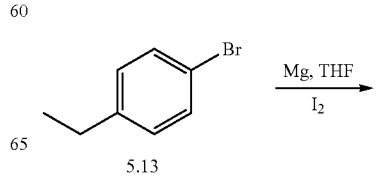

5.13

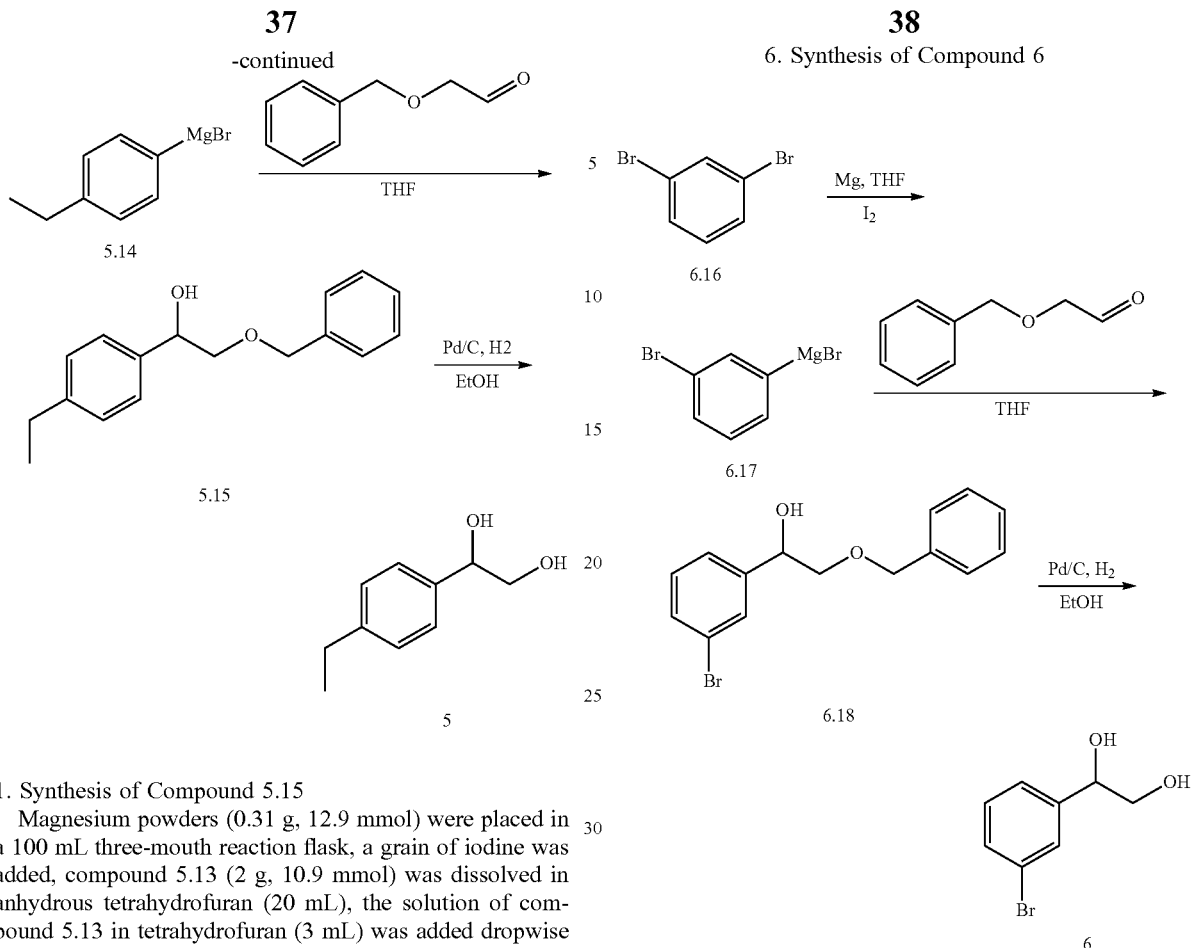

1. Synthesis of Compound 5.15

Magnesium powders (0.31 g, 12.9 mmol) were placed in a 100 mL three-mouth reaction flask, a grain of iodine was added, compound 5.13 (2 g, 10.9 mmol) was dissolved in anhydrous tetrahydrofuran (20 mL), the solution of compound 5.13 in tetrahydrofuran (3 mL) was added dropwise into a reaction bottle by a constant-pressure drop funnel, the reaction was initiated with a hair dryer, and the remaining 17 mL of the solution of compound 5.13 in tetrahydrofuran was slowly added dropwise after the reaction was started. Upon addition, the reaction was refluxed for 3.5 hours, and finally a solution of Compound 5.14 in tetrahydrofuran was obtained.

In an ice bath, the solution of compound 5.14 in tetrahydrofuran was added dropwise to a solution of benzyloxyacetaldehyde (1.62 g, 10.8 mmol) in anhydrous tetrahydrofuran (14 mL) solution. Upon addition, the reaction was raised to room temperature for 1 hour, and then a saturated aqueous solution of ammonium chloride was added to quench the reaction. Finally, tetrahydrofuran was removed and the residue was extracted with ethyl acetate, dried over anhydrous sodium sulfate, purified by a column (PE:EA=10:1) to give 1.4 g of the target compound with a two-step yield of 50%. $^1$H NMR (400 MHz, DMSO): δ 7.44-7.42 (m, 1H), 7.35-7.25 (m, 5H), 7.19-7.12 (m, 3H), 5.33 (d, J=4.4 Hz, 1H), 5.01-4.97 (m, 1H), 4.55-4.47 (m, 2H), 3.51-3.40 (m, 2H), 2.66 (m, 2H), 1.15 (t, J=7.6, 3H). LC-MS: 255.30 (M−H)⁻.

2. Synthesis of Compound 5

Compound 5.15 (1.2 g, 4.7 mmol) was dissolved in ethanol (15 mL) and 10% palladium carbon (0.3 g) was added, air was replaced with H$_2$, and the reaction system was stirred for 3 hours at 38° C. After the reaction was completed, the solvent was removed and the obtained residue was purified by a column (PE:EA=5:1) to give 0.43 g of target compound with a yield of 47%. $^1$H NMR (400 MHz, DMSO): δ 7.41-7.14 (m, 4H), 5.14 (d, J=4.0 Hz, 1H), 4.81-4.76 (m, 2H), 3.37 (q, J=7.6 Hz, 2H), 1.16 (t, J=7.6 Hz, 3H). LC-MS: 165.10 (M−H)⁻.

6. Synthesis of Compound 6

1. Synthesis of Compound 6.18

Magnesium powders (0.31 g, 12.9 mmol) were placed in a 100 mL three-mouth reaction flask, a grain of iodine was added, compound 6.16 (2 g, 8.5 mmol) was dissolved in anhydrous tetrahydrofuran (20 mL), the solution of compound 16 in tetrahydrofuran (3 mL) was added dropwise into a reaction bottle by a constant-pressure drop funnel, the reaction was initiated with an electric hair drier, the remaining 17 mL of the solution of compound 6.16 in tetrahydrofuran was slowly added dropwise after the reaction was started. Upon addition, the reaction was refluxed for 3.5 hours, and finally a solution of compound 6.17 in tetrahydrofuran was obtained.

In an ice bath, the solution of compound 6.17 in tetrahydrofuran was added dropwise to a solution of benzyloxyacetaldehyde (1.28 g, 8.5 mmol) in anhydrous tetrahydrofuran (14 mL). Upon addition, the reaction system was raised to room temperature for 1 hour, and then a saturated aqueous solution of ammonium chloride was added to quench the reaction. Finally, tetrahydrofuran was removed and the obtained residue was extracted with ethyl acetate, dried over anhydrous sodium sulfate, and purified by a column (PE:EA=10:1) to obtain 0.9 g of target compound with a yield of 32%. $^1$H NMR (400 MHz, DMSO): δ 7.38-7.02 (m, 9H), 5.33 (d, J=4.4 Hz, 1H), 4.75-4.70 (m, 1H), 4.47 (s, 2H), 3.56-3.49 (m, 2H). LC-MS: 307.30 (M−H)⁻.

2. Synthesis of Compound 6

Compound 6.18 (0.85 g, 2.8 mmol) was dissolved in ethanol (10 mL), 10% palladium carbon (0.23 g) was added, air was replaced with H$_2$, and the reaction system was stirred for 3 hours at 38° C. After the reaction was completed, the solvent was removed and the residue was purified by a column (PE:EA=5:1) to yield 0.2 g of target compound with a yield of 33%. $^1$H NMR (400 MHz, DMSO): δ 7.35-7.29 (m, 1H), 7.19-7.13 (m, 2H), 7.02-6.98 (m, 1H), 5.34 (d, J=4 Hz, 1H), 4.70 (t, J=6 Hz, 1H), 4.51 (q, J=5.6 Hz), 3.40 (t, J=6 Hz, 2H). LC-MS: 217.10 (M–H)$^-$.

Example 7. Synthesis of Compound 7

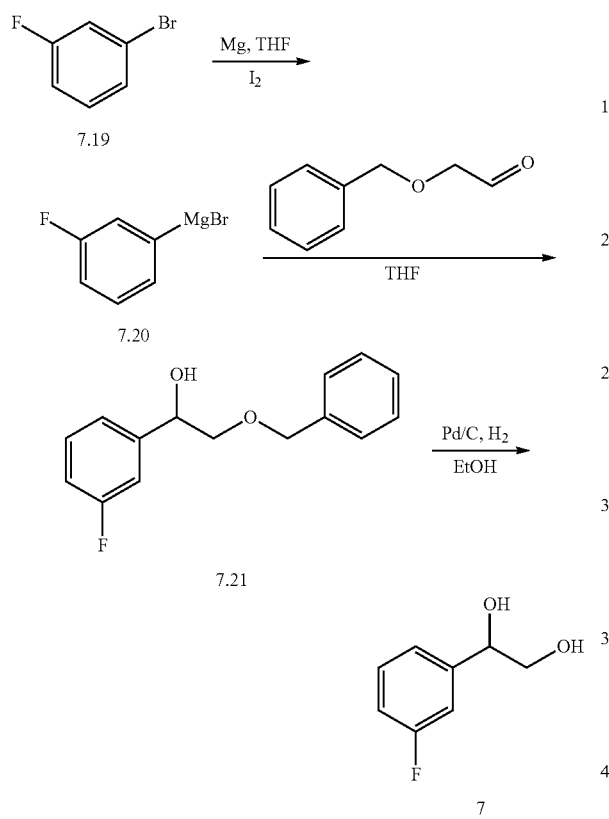

1. Synthesis of Compound 7.21

Magnesium powders (0.31 g, 12.9 mmol) were placed in a 100 mL three-mouth reaction flask, a grain of iodine was added, compound 7.19 (2 g, 11.7 mmol) was dissolved in anhydrous tetrahydrofuran (20 mL), the solution of compound 19 in tetrahydrofuran (3 mL) was added dropwise into a reaction bottle by a constant-pressure drop funnel, and the reaction was initiated with an electric hair drier. The remaining 7.17 mL of the solution of compound 7.19 in tetrahydrofuran was slowly added dropwise after the reaction was started. Upon addition, the reaction was refluxed for 3.5 hours, and finally a solution of compound 7.20 in tetrahydrofuran was obtained.

In an ice bath, the solution of compound 7.20 in tetrahydrofuran was added dropwise to a solution of benzyloxyacetaldehyde (1.76 g, 11.7 mmol) in anhydrous tetrahydrofuran (14 mL). Upon addition, the reaction system was raised to room temperature for 1 hour, and then a saturated aqueous solution of ammonium chloride was added to quench the reaction. Finally, tetrahydrofuran was removed and the obtained residue was extracted with ethyl acetate, dried over anhydrous sodium sulfate, and purified by a column (PE:EA=10:1) to obtain 1.32 g of target compound with a yield of 47.2%. $^1$H NMR (400 MHz, DMSO): δ 7.44-7.14 (m, 9H), 5.36 (d, J=4.4 Hz, 1H), 4.71-4.67 (m, 1H), 4.50 (s, 2H), 3.50-3.41 (m, 2H). LC-MS: 245.30 (M–H)$^-$ 2. Synthesis of Compound 7

Compound 7.21 (1.3 g, 5.4 mmol) was dissolved in ethanol (10 mL), 10% palladium carbon (0.23 g) was added, air was replaced with H$_2$, and the reaction was stirred for 3 hours at 38° C. After the reaction was completed, the solvent was removed and the residue was purified by a column (PE:EA=5:1) to yield 0.2 g of target compound with a yield of 33%. $^1$H NMR (400 MHz, DMSO): δ 7.37-7.31 (m, 1H), 7.18-7.12 (m, 2H), 7.06-7.01 (m, 1H), 5.39 (d, J=4.4 Hz, 1H), 4.77 (t, J=5.6 Hz, 1H), 4.56 (q, J=5.6 Hz), 3.43 (t, J=6 Hz, 2H). LC-MS: 155.10 (M–H)$^-$.

Example 8. Synthesis of Compound 8

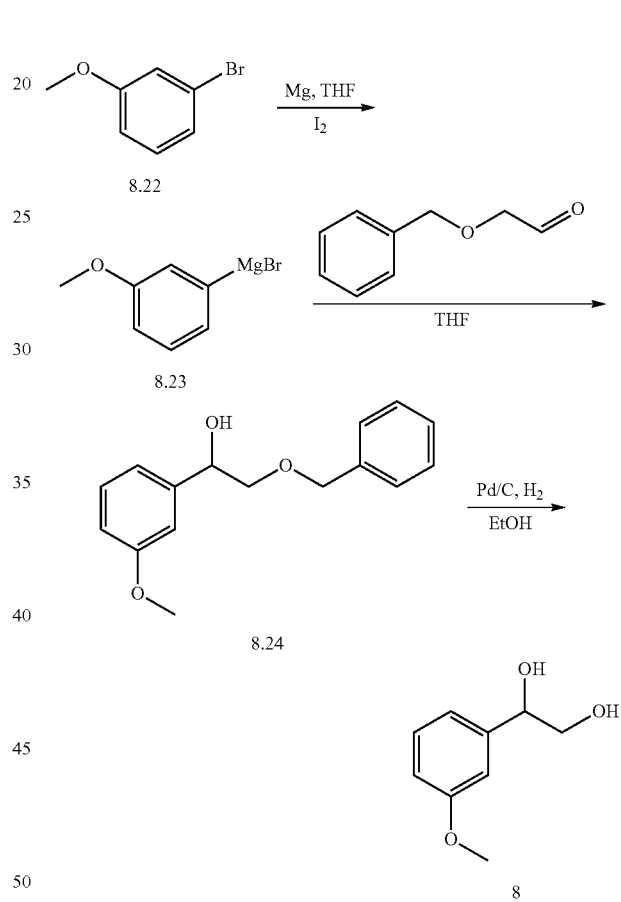

1. Synthesis of Compound 8.24

Magnesium powders (0.57 g, 22.2 mmol) were placed in a 100 mL three-mouth reaction flask, a grain of iodine was added, compound 8.22 (4 g, 21.5 mmol) was dissolved in anhydrous tetrahydrofuran (40 mL), the solution of compound 8.22 in tetrahydrofuran (5 mL) was added dropwise into a reaction bottle by a constant-pressure drop funnel, and the reaction was initiated with an electric hair drier. The remaining 35 mL of the solution of compound 8.22 in tetrahydrofuran was slowly added dropwise after the reaction was started. Upon addition, the reaction was refluxed for 3.5 hours, and finally a solution of compound 8.23 in tetrahydrofuran was obtained.

In an ice bath, the solution of compound 8.23 in tetrahydrofuran was added dropwise to a solution of benzyloxyacetaldehyde (3.21 g, 21.5 mmol) in anhydrous tetrahydrofuran (30 mL). Upon addition, the reaction system was raised to room temperature for 1 hour, and then a saturated aqueous solution of ammonium chloride was added to quench the reaction. Finally, tetrahydrofuran was removed and the obtained residue was extracted with ethyl acetate, dried over anhydrous sodium sulfate, and purified by a column (PE:EA=10:1) to obtain 4 g of target compound with a yield of 63.6%. ¹H NMR (400 MHz, DMSO): δ 7.35-7.14 (m, 9H), 5.33 (d, J=4.0 Hz, 1H), 4.74-4.70 (m, 1H), 4.51 (s, 2H), 3.73 (s, 3H), 3.52-3.43 (m, 2H). LC-MS: 257.30 (M−H)⁻.

2. Synthesis of Compound 8

Compound 8.24 (3.5 g, 13.6 mmol) was dissolved in ethanol (30 mL), 10% palladium carbon (0.69 g) was added, air was replaced with H₂, and the reaction was stirred for 3 hours at 38° C.

After the reaction was completed, the solvent was removed and the residue was purified by a column (PE:EA=5:1) to yield 1.42 g of target compound with a yield of 62.3%. ¹H NMR (400 MHz, DMSO): δ 7.23 (t, J=8 Hz, 1H), 6.91 (d, J=7.6 Hz, 2H), 6.80-6.77 (m, 1H), 5.24 (d, J=4.4 Hz, 1H), 4.73 (t, J=5.6 Hz, 1H), 4.53 (q, J=4.8 Hz, 1H), 3.73 (s, 3H), 3.43-3.36 (m, 2H). LC-MS: 167.10 (M−H)⁻.

Example 9. Synthesis of Compound 9

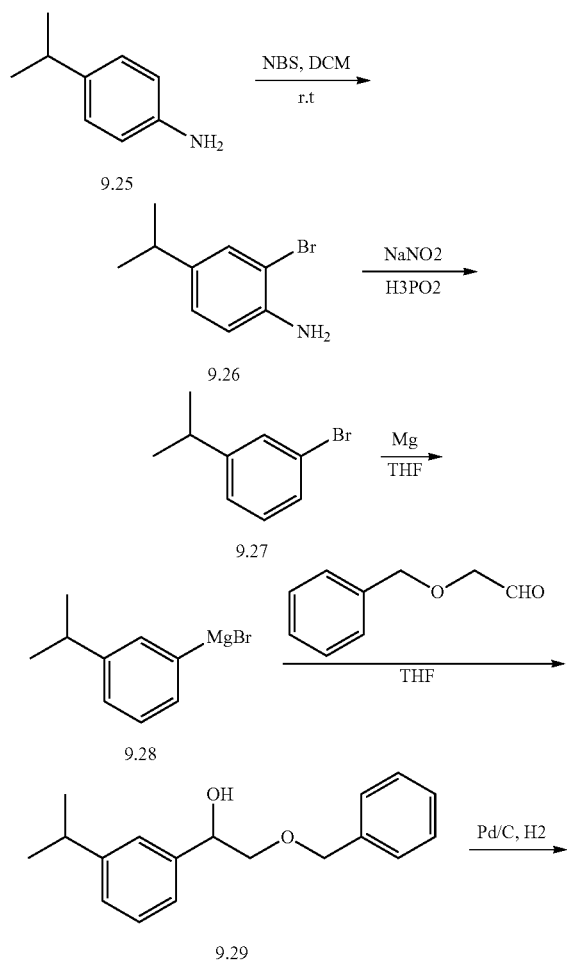

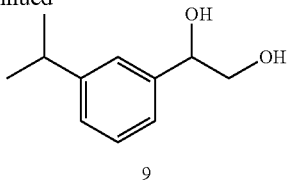

1. Synthesis of Compound 9.26 p-isopropylaniline (4 g, 29.6 mmol) was dissolved in dichloromethane (40 ml), and NBS (5.8 g, 32.6 mmol) was added to a dichloromethane solution in batches under an ice bath. The reaction was raised to room temperature, and the reaction was completed after 1 hour. After purification, 4.6 g of the product was obtained with a yield of 74%. ¹H NMR (400 MHz, CDCl₃): δ 7.28 (d, J=1.6 Hz, 1H), 6.98 (dd, J₁=1.6 Hz, J₂=1.6 Hz, 1H), 6.71 (d, J=8 Hz, 1H), 3.76 (s, 2H), 2.79 (m, 1H), 1.20 (d, J=6.8 Hz, 6H). LC-MS: 214.10 (M+H)⁺.

2. Synthesis of Compound 9.27

Compound 9.26 (2 g, 9.3 mmol) was dissolved in a mixed solution of acetic acid (10 mL), water (4 mL) and concentrated HCl (1 mL), and 2 mL of an aqueous solution of NaNO₂ (0.78 g, 11.2 mmol) was added dropwise to the above mixed solution in an ice bath. After half an hour, in an ice bath, the resulting reaction mixture was added dropwise to a 50% H₃PO₂ aqueous solution (12 mL). Upon addition, the reaction was continued for 8 hours, and then the reaction temperature was increased to 25 degrees Celsius for 3 days. After the reaction was completed, the reaction mixture was purified by a column to obtain 1.4 g of the product with a yield of 75.3%. ¹H NMR (400 MHz, DMSO): δ 7.42 (s, 1H), 7.37-7.34 (m, 1H), 7.25 (d, J=4.8 Hz, 2H), 1.20 (d, J=6.8 Hz, 6H). LC-MS: 199.20 (M+H)⁺.

3. Synthesis of Compound 9.29

Magnesium powders (0.17 g, 7.1 mmol) were placed in a 100 mL three-mouth reaction flask, a grain of iodine was added, compound 9.27 (1.3 g, 7.5 mmol) was dissolved in anhydrous tetrahydrofuran (12 mL), the solution of compound 9.27 in tetrahydrofuran (2 mL) was added dropwise into a reaction bottle by a constant-pressure drop funnel, and the reaction was initiated with an electric hair drier. The remaining 10 mL of the solution of compound 9.27 in tetrahydrofuran was slowly added dropwise after the reaction was started. Upon addition, the reaction was refluxed for 3.5 hours, and finally a solution of compound 9.28 in tetrahydrofuran was obtained.

In an ice bath, the solution of compound 9.28 in tetrahydrofuran was added dropwise to a solution of benzyloxyacetaldehyde (0.98 g, 7.1 mmol) in anhydrous tetrahydrofuran (10 mL). Upon addition, the reaction system was raised to room temperature for 1 hour, and then a saturated aqueous solution of ammonium chloride was added to quench the reaction. Finally, tetrahydrofuran was removed and the obtained residue was extracted with ethyl acetate, dried over anhydrous sodium sulfate, and purified by a column (PE:EA=10:1) to obtain 1 g of target compound with a yield of 56%. ¹H NMR (400 MHz, DMSO): δ 7.36-7.15 (m, 8H), 7.09 (d, J=8 Hz, 1H), 5.38 (d, J=4 Hz, 1H), 4.74-4.70 (m, 1H), 4.51 (s, 2H), 3.53-3.44 (m, 2H), 2.83-2.76 (m, 1H), 1.20 (d, J=7.6 Hz, 6H). LC-MS: 271.30 (M+H)⁺.

4. Synthesis of Compound 9

Compound 9.28 (1 g, 3.6 mmol) was dissolved in ethanol (10 mL), 10% palladium carbon (0.19 g) was added, air was replaced with H₂, and the reaction was stirred for 3 hours at 38° C. After the reaction was completed, the solvent was removed and the residue was purified by a column (PE:EA=5:1) to yield g of target compound with a yield of %. $^1$H NMR (400 MHz, CDCl$_3$): δ 7.19-7.04 (m, 4H), 4.69 (d, J=4.0 Hz, 1H), 3.64-3.52 (m, 2H), 3.22 (s, 2H), 2.83-2.76 (m, 1H), 1.15 (d, J=7.6 Hz, 6H). LC-MS: 179.10 (M−H)$^-$.

Example 10. Synthesis of Compound 10

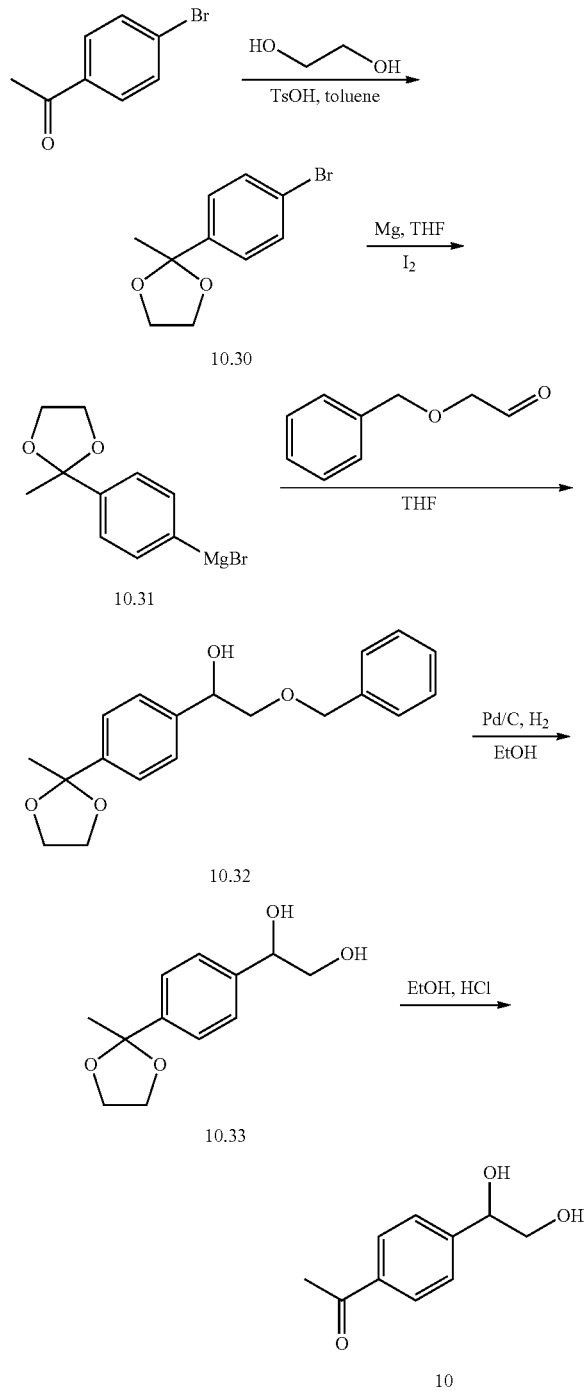

1. Synthesis of Compound 10.30 (Protection on Carbonyl)

p-Bromoacetophenone (5 g, 25.4 mmol) was taken into a 100 mL three-necked flask, toluene (60 mL) was added as a solvent, ethylene glycol (10 g, 161.3 mmol) and p-toluenesulfonic acid (1 g, 5 mmol) were added, the temperature was raised to 130° C., and the reaction was refluxed for 16 h. After the reaction was completed, brine was added, stirred, and stood for separating layers. The organic phase was taken, dried over anhydrous sodium sulfate, and subjected to column chromatography to obtain 3 g of compound with a yield of 48%. $^1$H NMR (400 MHz, CDCl$_3$): δ 7.49-7.44 (m, 2H), δ 7.37-7.34 (m, 2H), 4.05 (m, 2H), 3.77-3.73 (m, 2H), 1.62 (s, 3H). LC-MS: 242.10 (M−H)$^-$.

2. Synthesis of Compound 10.32

Magnesium powders (0.31 g, 12.9 mmol) were placed in a 100 mL three-mouth reaction flask, a grain of iodine was added, 4-bromobenzene ethylene ketal (2.5 g, 10.4 mmol) was dissolved in anhydrous tetrahydrofuran (20 mL), the solution of ketal in tetrahydrofuran (3 mL) was added dropwise into the reaction bottle by a constant-pressure drop funnel, and the reaction was initiated with an electric hair drier. The remaining 17 mL of the solution in tetrahydrofuran was slowly added dropwise after the reaction was started. Upon addition, the reaction was refluxed for 3.5 hours, and finally a solution of Grignard reagent in tetrahydrofuran was obtained.

In an ice bath, the solution of ketal in tetrahydrofuran was added dropwise to a solution of benzyloxyacetaldehyde (1.5 g, 10 mmol) in anhydrous tetrahydrofuran (14 mL). Upon addition, the reaction system was raised to room temperature for 1 hour, and then a saturated aqueous solution of ammonium chloride was added to quench the reaction. Finally, tetrahydrofuran was removed and the obtained residue was extracted with ethyl acetate, dried over anhydrous sodium sulfate, and purified by a column (PE:EA=10:1) to obtain 0.8 g of target compound with a yield of 25%. $^1$H NMR (400 MHz, CDCl$_3$): δ 7.44-7.29 (m, 10H), 4.90 (dd, J=8.8 Hz, 3.2 Hz, 1H), 4.57 (q, J=12 Hz, 2H), 3.98 (t, J=6 Hz, 2H), 3.71 (t, J=6 Hz, 2H), 3.60 (dd, J=8 Hz, 3.2 Hz), 3.39 (t, J=8 Hz, 1H), 1.62 (s, 3H). LC-MS: 313.20 (M−H)$^-$.

3. Synthesis of Compound 10.33 (Debenzylation)

Compound (0.75 g, 2.4 mmol) was dissolved in ethanol (10 mL), 10% palladium carbon (0.23 g) was added, air was replaced with H$_2$, and the reaction was stirred for 3 hours at 38° C. After the reaction was completed, the solvent was removed and the residue was purified by a column (PE:EA=5:1) to get 0.2 g of target compound with a yield of 29%. $^1$H NMR (400 MHz, DMSO): δ 7.35-7.29 (m, 4H), 5.23 (d, J=4 Hz, 1H), 4.74 (t, J=6 Hz, 1H), 4.54-4.49 (m, 1H), 3.98-3.94 (m, 2H), 3.43 (t, J=6.8 Hz, 2H), 1.53 (s, 3H). LC-MS: 223.10 (M−H)$^-$.

4. Synthesis of Compound 10

The compound (0.18 g, 0.8 mmol) was taken, 10 mL of ethanol was added, hydrochloric acid for 5 d. The reaction was conducted at 50° C. for 15 h. Water was added, and the obtained mixture was extract with DCM. The organic phase was dried over anhydrous sodium sulfate, and purified through column chromatography to obtain 0.06 g of product with a yield of 40%. $^1$H NMR (400 MHz, DMSO): δ 7.91 (d, J=8.4 Hz, 2H), 7.49 (d, J=8.4 Hz, 2H), 5.42 (d, J=4 Hz, 1H), 4.80 (t, J=6 Hz, 1H), 4.63 (q, J=5.6 Hz, 1H), 3.46 (t, J=6 Hz, 2H), 2.56 (s, 3H). LC-MS: 181.10 (M+H)$^+$.

Example 11. Synthesis of Compound 11(D)

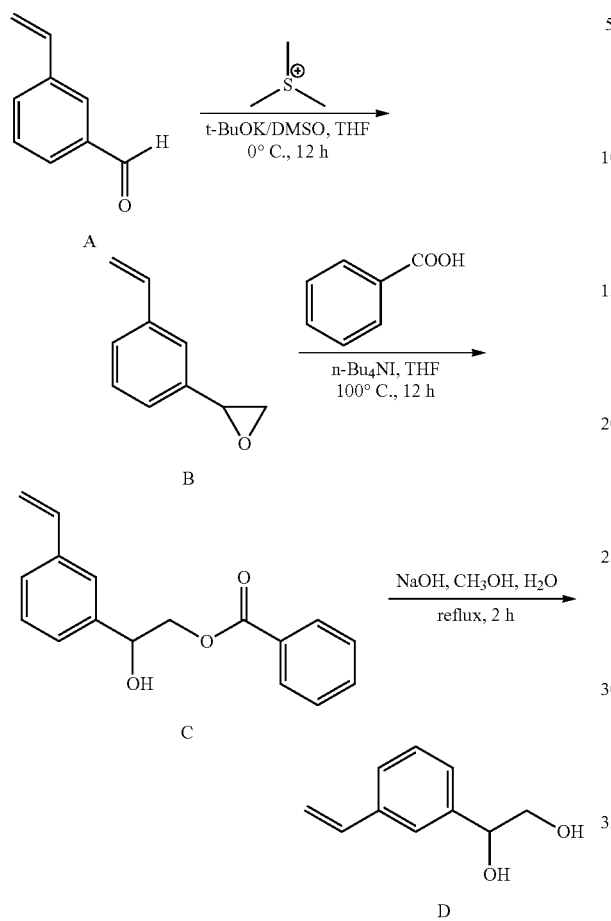

1. Synthesis of 3-vinylphenyl Ethylene Oxide (B)

Under the protection of nitrogen, potassium tert-butoxide (2.214 g, 0.02 mol), THF (2 ml), DMSO (12 ml) was added dropwise in a three-necked flask containing trivinylbenzaldehyde (A, 1.215 g, 0.009 mol), trimethylsulfur iodide (2.118 g, 0.011 mol), THF (8 ml) and DMSO (15 ml). The reaction was conducted in an ice bath for 12 h. During the reaction, TLC was used to monitor the progress of the reaction. After the reaction was completed, the reaction mixture was extracted with dichloromethane, and the organic layer was dried over anhydrous sodium sulfate, and finally purified by column chromatography (PE:EA=150:1) to obtain 0.755 g of 3-vinylphenylethylene oxide (B) (56%). $^1$H NMR (DMSO, 400 MHz): δ 7.43-7.21 (m, 4H), 6.77 (dd, J=10.8 17.7 Hz, 1H,), 5.83 (d, J=17.7 Hz, 1H), 5.29 (d, J=10.8 Hz, 1H), 3.93 (dd, J=2.7, 4.0 Hz, 1H), 3.13 (dd, J=4.0, 5.5 Hz, 1H,), 2.88 (q, J=2.7 Hz, 1H).

2. Synthesis of 3-(1-hydroxy-2-benzoyloxyethyl)styrene (C)

Under the protection of nitrogen, benzoic acid (1.22 g, 10.0 mmol), tetrabutylammonium iodide (0.369 g, 1.0 mmol), and 3-vinylphenyl ethylene oxide (B, 1.46 g, 10.0 mmol) in 5 mL of DMF. The reaction was conducted at 100° C. for 12 h. During the reaction, TLC was used to monitor the progress of the reaction. After the reaction was completed, the reaction mixture was extracted with dichloromethane, and the organic layer was dried over anhydrous sodium sulfate, and finally purified by column chromatography (PE:EA=10:1) to obtain 3-(1-hydroxy-2-benzoyloxyethyl)styrene (C) 0.818 g (30.47%). $^1$H NMR (DMSO, 400 MHz): δ 7.33-7.95 (m, 9H), 6.78 (dd, J=10.9, 17.6 Hz, 1H), 5.85 (d, J=17.6 Hz, 1H), 5.78 (d, J=4.6 Hz, 1H), 5.27 (d, J=10.9, 1H), 4.96 (q, J=4.6, 1H), 4.34 (d, J=5.7 Hz, 2H).

3. Synthesis of Compound 11(D)

3-(1-hydroxy-2-benzoyloxyethyl)styrene (C, 0.20 g, 0.745 mmol) and sodium hydroxide (0.043 g, 1.08 mmol) in 4 ml of methanol, and refluxed for 2 h. And then 1 ml of $H_2O$ was added. During the reaction, TLC was used to monitor the progress of the reaction. After the reaction was completed, the reaction mixture was extracted with dichloromethane, and the organic layer was dried over anhydrous sodium sulfate, and finally purified by column chromatography (PE:EA=1:1) to obtain 3-(1,2-dihydroxyethyl)styrene (D) 0.07 g (57.2%). $^1$H NMR (CDCl3, 400 MHz): δ 7.12-7.29 (m, 4H), 6.65 (dd, J=11.1, 17.7 Hz, 1H), 5.69 (d, J=17.7 Hz, 1H), 5.19 (d, J=11.1 Hz, 1H), 4.71 (dd, J=3.3, 8.3 Hz, 1H), 3.65 (m, 2H), 3.07 (s, 2H). MS (EI): 164.1.

Example 12. Synthesis of Compound 30

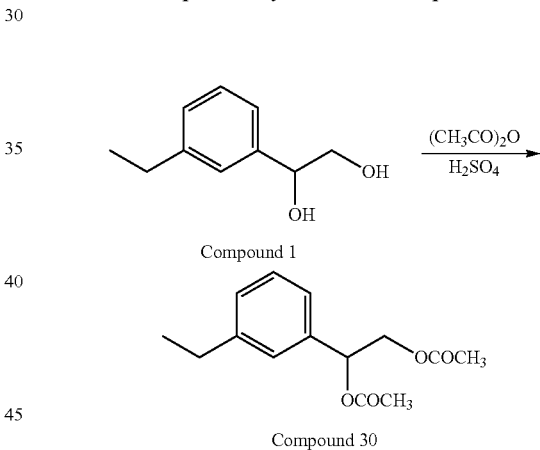

Compound 1 (1.66 g, 0.01 mol) was dissolved in 7 mL of DCM, 1 drop of concentrated sulfuric acid was added, and the exothermic reaction was initiated by slightly heating. After the reaction was completed, 20 mL of solvent was added, washed with sodium bicarbonate solution, dried, concentrated, and purified by a column (PE:EA=10:1) to obtain 2.00 g of the target compound with a yield of 80%. $^1$H NMR (400 MHz, CDCl$_3$): δ 7.21-7.00 (m, 4H), 4.75 (dd, J$_1$=8.0 Hz, J$_2$=3.6 Hz, 1H), 3.72-3.60 (m, 2H), 2.66 (q, J=7.6 Hz, 2H), 2.21 (s, 3H), 2.10 (s, 3H), 1.25 (t, J=7.6 Hz, 3H). LC-MS: 251.17 (M+H)$^+$.

Example 13 Antihypertensive Activity Test

In this example, whether the compound of the present invention exhibits lowering effects on the blood pressure of spontaneously hypertensive rats (SHR) and the effects on the heart rate were tested according to conventional experimental procedures in the art.

Tested Drugs: Compounds of the Invention. The dosage of all compound was uniformly set to 200 mg/kg.

Other reagents, test animals, and instruments: All other reagents and instruments used in this example are commercially available reagents and instruments.

In the test, changes in the blood pressure before and after the administration were detected, and compared with the basic value, a reduction of SBP ≥20 mmHg after administration was judged as effective antihypertensive effects; and at the same time, changes in the heart rate before and after the administration were detected.

Statistical Analysis:

Heart rate was expressed as mean±standard deviation ($\bar{x}\pm s$). The changes of heart rate before and after the administration were compared by using Two-sample equal variance paired t test, and P<0.05 was regarded as the standard of statistically significant difference.

Experimental Results

In contrast, the positive drug metoprolol hydrochloride exhibits the best blood pressure-reducing effects. After administration, the blood pressure was reduced by more than 20 mmHg at most recorded time points, and the lowest value of blood pressure was recorded at 3 hours after administration. Metoprolol hydrochloride can significantly slow down the heart rate while lowering blood pressure. 6 hours after administration, the average heart rate was slowed by 46 beats/min. This characteristic of both reducing blood pressure and slowing heart rate comply with pharmacological effects of p receptor-blocking drug.

Secondly, the compound with antihypertensive effects was 1-(3-ethylphenyl)-1,2-ethylene glycol. Before and after administration, the antihypertensive duration of 1-(3-ethylphenyl)-1,2-ethylene glycol was similar to that of the positive drug metoprolol hydrochloride, and the maximum antihypertensive effects was also observed at 3 h after administration, however, the reduction amplitude in blood pressure was slightly lower than that of the positive drug metoprolol hydrochloride. In addition, effects of 1-(3-ethylphenyl))-1,2-ethylene glycol on heart rate was just the opposite of that of the positive drug Metoprolol Hydrochloride, which can significantly increase heart rate while lowering blood pressure.

TABLE 1

Effects of several compounds on SHR blood pressure and heart rate before and after administration (6 h M ± SD) n = 8

| Compound No. | Group (structure) | Dosage (mg/kg) | Blood pressure (SBP, mmHg) | |
|---|---|---|---|---|
| | | | Baseline | After administration |
| Metoprolol Hydrochloride | 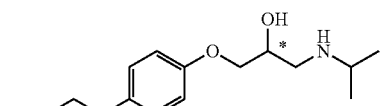 | 200 | 186 ± 7.87 | 164 ± 7.85 |
| compound 4 | 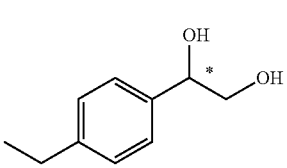 | 200 | 184 ± 14.7 | 181 ± 13.2 |
| compound 1 | 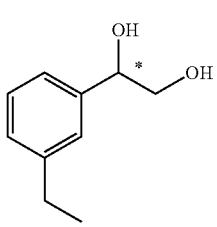 | 200 | 192 ± 7.98 | 174 ± 4.01 |
| compound 12 | 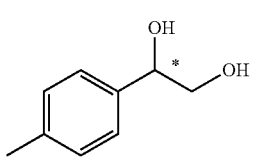 | 200 | 187 ± 11.9 | 181 ± 8.80 |

TABLE 1-continued

Effects of several compounds on SHR blood pressure and heart rate before and after administration (6 h M ± SD) n = 8

| compound 13 | [structure: 1-(3-(hydroxymethyl)phenyl)propan-1-ol with * at chiral carbon] | 200 | 190 ± 13.2 | 178 ± 11.2 |
|---|---|---|---|---|

| Compound No. | Difference mmHg | Heart rate (beat/min) | | Difference (beat/min) |
|---|---|---|---|---|
| | | Baseline | After administration | |
| Metoprolol Hydrochloride | 23 | 328 ± 24.5 | 282 ± 21.3 | −46 |
| compound 4 | 3 | 345 ± 42.2 | 346 ± 43.4 | 1 |
| compound 1 | 18 | 356 ± 46.4 | 368 ± 25.5 | 12 |
| compound 12 | 6 | 333 ± 44.0 | 336 ± 49.5 | 3 |
| compound 13 | 12 | 319 ± 21.0 | 329 ± 27.7 | 10 |

The experimental results of the effects of other compounds on lowering blood pressure and accelerating heart rate are shown in Table 2, Table 3, and Table 4.

TABLE 2

Dynamic changes in SHR blood pressure after administration of several compounds and the difference before and after administration (SBP, mmHg)n = 8

| Group | Time after administration (h) | | | | | | |
|---|---|---|---|---|---|---|---|
| | 0 | 1 | 2 | 3 | 4 | 5 | 6 |
| [structure] Metoprolol Hydrochloride | 186 ± 7.24 | 166 ± 6.39 | 164 ± 4.50 | 161 ± 9.15 | 163 ± 13.7 | 164 ± 15.9 | 168 ± 8.78 |
| Difference | | 20 | 22 | 25 | 24 | 23 | 18 |
| [structure] Compound 4 | 184 ± 14.7 | 182 ± 11.6 | 178 ± 10.8 | 177 ± 10.9 | 180 ± 15.80 | 184 ± 16.0 | 186 ± 17.7 |
| Difference | | 3 | 7 | 8 | 5 | 1 | −1 |
| [structure] Compound 1 | 192 ± 7.98 | 176 ± 9.55 | 172 ± 7.36 | 169 ± 4.07 | 173 ± 7.15 | 175 ± 5.61 | 180 ± 6.66 |
| Difference | | 16 | 20 | 23 | 19 | 17 | 11 |

TABLE 2-continued

Dynamic changes in SHR blood pressure after administration of several
compounds and the difference before and after administration (SBP, mmHg)n = 8

| Group | Time after administration (h) | | | | | | |
|---|---|---|---|---|---|---|---|
| | 0 | 1 | 2 | 3 | 4 | 5 | 6 |
| Compound 12 (1-(4-methylphenyl)ethane-1,2-diol) | 187 ± 11.9 | 184 ± 10.6 | 182 ± 10.4 | 183 ± 9.90 | 178 ± 6.61 | 182 ± 7.25 | 184 ± 12.1 |
| Difference | | 3 | 5 | 4 | 9 | 5 | 3 |
| Compound 13 (1-(3-(hydroxymethyl)phenyl)propan-1-ol) | 190 ± 13.2 | 186 ± 12.4 | 178 ± 12.0 | 171 ± 13.1 | 176 ± 11.4 | 180 ± 11.9 | 176 ± 10.1 |
| Difference | | 3 | 12 | 19 | 14 | 10 | 14 |

TABLE 3

Dynamic changes in SHR heart rate after administration and difference before
and after administration (beat/min) N = 8

| Group | Time after administration (h) | | | | | | |
|---|---|---|---|---|---|---|---|
| | 0 | 1 | 2 | 3 | 4 | 5 | 6 |
| Metoprolol Hydrochloride | 328 ± 24.5 | 283 ± 24.4 | 283 ± 23.1 | 279 ± 22.3 | 280 ± 23.0 | 285 ± 24.0 | 288 ± 28.5 |
| Difference | | −44 | −45 | −49 | −48 | −43 | −40 |
| Compound 4 (1-(4-ethylphenyl)ethane-1,2-diol) | 345 ± 42.2 | 347 ± 42.6 | 349 ± 49.7 | 349 ± 48.3 | 345 ± 45.1 | 338 ± 39.7 | 341 ± 46.9 |
| Difference | | 2 | 4 | 4 | 0 | −6 | −4 |
| Compound 1 (1-(3-ethylphenyl)ethane-1,2-diol) | 356 ± 46.4 | 348 ± 39.3 | 380 ± 34.1 | 385 ± 31.5 | 385 ± 30.4 | 372 ± 28.5 | 373 ± 31.3 |
| Difference | | −9 | 23 | 28 | 28 | 16 | 17 |

TABLE 3-continued

Dynamic changes in SHR heart rate after administration and difference before
and after administration (beat/min) N = 8

| Group | Time after administration (h) | | | | | | |
|---|---|---|---|---|---|---|---|
| | 0 | 1 | 2 | 3 | 4 | 5 | 6 |
| Compound 12 (4-methyl-phenyl-1,2-ethanediol) | 333 ± 44.0 | 328 ± 47.6 | 342 ± 46.9 | 348 ± 53.2 | 336 ± 54.5 | 331 ± 51.0 | 336 ± 52.7 |
| Difference | | −5 | 8 | 15 | 3 | −3 | 3 |
| Compound 13 (3-hydroxymethyl-phenyl-1-propanol) | 319 ± 21.0 | 325 ± 24.2 | 332 ± 38.9 | 335 ± 43.8 | 334 ± 45.8 | 329 ± 39.5 | 320 ± 43.1 |
| Difference | | 6 | 14 | 17 | 15 | 10 | 2 |

TABLE 4

Dynamic changes in SHR blood pressure after administration and difference
before and after administration (SBP, mmHg) n = 8

| Group | Time after administration (h) | | | | | | |
|---|---|---|---|---|---|---|---|
| | 0 | 1 | 2 | 3 | 4 | 5 | 6 |
| Compound 2 (phenyl-1,2-ethanediol) | 185 ± 7.25 | 169 ± 6.39 | 167 ± 4.50 | 166 ± 9.15 | 166 ± 13.7 | 165 ± 15.3 | 170 ± 8.77 |
| Difference | | 16 | 18 | 19 | 19 | 20 | 15 |
| Compound 3 (3-methyl-phenyl-1,2-ethanediol) | 188 ± 14.5 | 180 ± 11.6 | 178 ± 10.9 | 177 ± 13.9 | 180 ± 15.80 | 186 ± 16.0 | 186 ± 17.7 |
| Difference | | 18 | 10 | 11 | 8 | 2 | 2 |
| Compound 7 (3-fluoro-phenyl-1,2-ethanediol) | 193 ± 7.90 | 177 ± 9.56 | 172 ± 7.36 | 171 ± 4.07 | 173 ± 6.18 | 175 ± 5.63 | 180 ± 7.61 |
| Difference | | 16 | 21 | 22 | 20 | 18 | 13 |
| Compound 6 (3-bromo-phenyl-1,2-ethanediol) | 189 ± 11.2 | 184 ± 10.9 | 180 ± 12.4 | 180 ± 7.80 | 183 ± 6.56 | 182 ± 8.29 | 188 ± 13.2 |
| Difference | | 5 | 9 | 9 | 6 | 7 | 1 |

TABLE 4-continued

Dynamic changes in SHR blood pressure after administration and difference before and after administration (SBP, mmHg) n = 8

| Group | Time after administration (h) | | | | | | |
|---|---|---|---|---|---|---|---|
| | 0 | 1 | 2 | 3 | 4 | 5 | 6 |
| 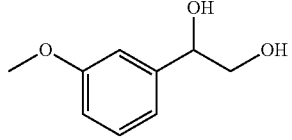<br>Compound 8<br>Difference | 194 ± 13.5<br><br>0 | 188 ± 12.4<br><br>6 | 181 ± 12.7<br><br>13 | 176 ± 11.1<br><br>18 | 176 ± 10.3<br><br>18 | 180 ± 11.3<br><br>14 | 186 ± 10.4<br><br>8 |
| 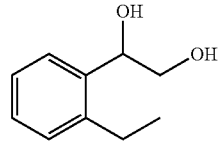<br>Compound 5<br>Difference | 189 ± 8.42 | 169 ± 6.32<br><br>20 | 174 ± 4.56<br><br>15 | 171 ± 9.34<br><br>18 | 173 ± 13.66<br><br>16 | 174 ± 15.9<br><br>15 | 178 ± 8.48<br><br>11 |
| 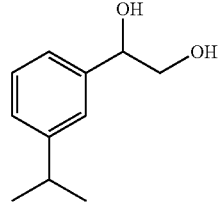<br>Compound 9<br>Difference | 194 ± 11.4 | 192 ± 11.6<br><br>2 | 188 ± 12.1<br><br>6 | 177 ± 12.3<br><br>17 | 180 ± 12.85<br><br>14 | 184 ± 16.0<br><br>10 | 186 ± 17.8<br><br>8 |
| 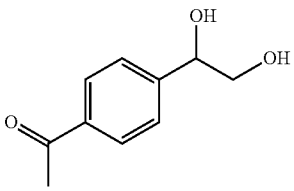<br>Compound 10<br>Difference | 192 ± 7.98 | 186 ± 9.54<br><br>6 | 182 ± 7.36<br><br>10 | 179 ± 4.07<br><br>13 | 183 ± 7.65<br><br>9 | 185 ± 5.64<br><br>7 | 190 ± 6.54<br><br>2 |
| 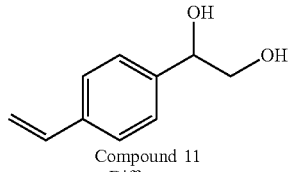<br>Compound 11<br>Difference | 189 ± 8.9 | 184 ± 10.8<br><br>5 | 182 ± 10.4<br><br>7 | 183 ± 9.90<br><br>6 | 178 ± 6.21<br><br>11 | 182 ± 7.45<br><br>7 | 184 ± 9.5<br><br>5 |
| 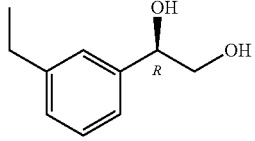<br>Compound 1-1<br>Difference | 190 ± 13.2<br><br>0 | 176 ± 12.4<br><br>14 | 168 ± 12.0<br><br>22 | 161 ± 13.1<br><br>29 | 166 ± 11.4<br><br>24 | 170 ± 11.9<br><br>20 | 186 ± 10.1<br><br>14 |
| 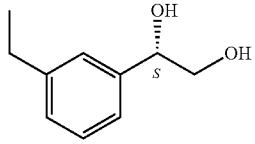<br>Compound 1-2<br>Difference | 186 ± 7.24 | 176 ± 6.39<br><br>10 | 164 ± 4.50<br><br>22 | 161 ± 9.15<br><br>25 | 163 ± 13.7<br><br>23 | 174 ± 15.9<br><br>12 | 178 ± 8.78<br><br>8 |

TABLE 4-continued

Dynamic changes in SHR blood pressure after administration and difference before and after administration (SBP, mmHg) n = 8

| Group | Time after administration (h) | | | | | | |
|---|---|---|---|---|---|---|---|
| | 0 | 1 | 2 | 3 | 4 | 5 | 6 |
| 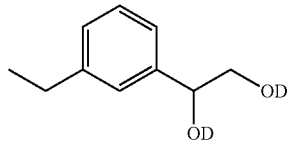<br>Compound 1-3 | 186 ± 7.24 | 168 ± 6.39 | 165 ± 4.50 | 163 ± 9.15 | 163 ± 13.7 | 164 ± 15.9 | 168 ± 8.78 |
| Difference | | 18 | 21 | 23 | 23 | 22 | 18 |
| 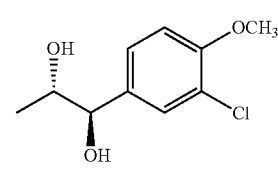<br>Compound 14 | 184 ± 14.7 | 182 ± 11.6 | 178 ± 10.8 | 177 ± 10.9 | 18 ± 15.80 | 184 ± 16.0 | 186 ± 17.7 |
| Difference | | 3 | 7 | 8 | 5 | 1 | −1 |
| 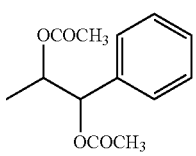<br>Compound 15 | 190 ± 7.98 | 176 ± 9.55 | 172 ± 7.36 | 169 ± 4.07 | 173 ± 7.15 | 175 ± 5.61 | 180 ± 6.66 |
| Difference | | 14 | 18 | 21 | 17 | 15 | 10 |
| 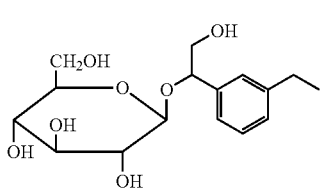<br>Compound 16 | 183 ± 11.9 | 174 ± 10.6 | 172 ± 10.4 | 173 ± 9.90 | 168 ± 6.61 | 172 ± 7.25 | 174 ± 12.1 |
| Difference | | 9 | 11 | 10 | 15 | 11 | 9 |
| 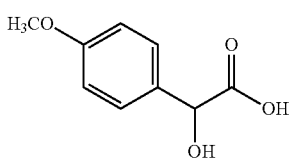 [SMILES: COc1ccc(C(O)C(=O)O)cc1]<br>Compound 17 | 195 ± 13.2 | 186 ± 12.4 | 188 ± 12.0 | 181 ± 13.1 | 186 ± 11.4 | 180 ± 11.9 | 186 ± 10.1 |
| Difference | 0 | 9 | 7 | 14 | 9 | 15 | 9 |
| 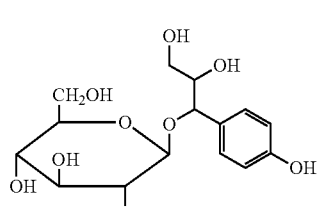<br>Compound 18 | 192 ± 7.24 | 176 ± 6.39 | 174 ± 4.50 | 171 ± 9.15 | 173 ± 13.7 | 174 ± 15.9 | 178 ± 8.78 |
| Difference | | 16 | 18 | 21 | 19 | 18 | 14 |

TABLE 4-continued
Dynamic changes in SHR blood pressure after administration and difference before and after administration (SBP, mmHg) n = 8
| Group | Time after administration (h) | | | | | | |
|---|---|---|---|---|---|---|---|
| | 0 | 1 | 2 | 3 | 4 | 5 | 6 |
| 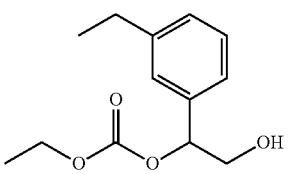 [SMILES: CCOC(=O)OC(CO)c1cccc(CC)c1] Compound 19 | 194 ± 14.7 | 182 ± 11.6 | 178 ± 10.8 | 177 ± 10.9 | 181 ± 15.80 | 184 ± 16.0 | 186 ± 17.7 |
| Difference | | 12 | 16 | 17 | 13 | 10 | 8 |
| 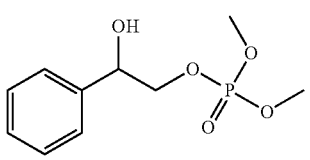 [SMILES: COP(=O)(OC)OCC(O)c1ccccc1] Compound 20 | 192 ± 7.98 | 186 ± 9.55 | 182 ± 7.36 | 189 ± 4.07 | 183 ± 7.15 | 185 ± 5.61 | 190 ± 6.66 |
| Difference | | 6 | 10 | 3 | 9 | 7 | 2 |
| 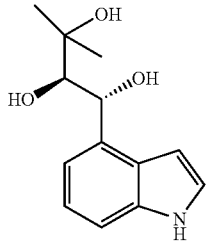 Compound 21 | 195 ± 11.9 | 184 ± 10.6 | 182 ± 10.4 | 183 ± 9.90 | 178 ± 6.61 | 182 ± 7.25 | 184 ± 12.1 |
| Difference | | 11 | 13 | 12 | 17 | 13 | 11 |
| 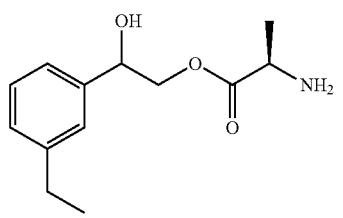 [SMILES: CCc1cccc(C(O)COC(=O)[C@@H](C)N)c1] Compound 22 | 198 ± 8.20 | 187 ± 6.39 | 184 ± 4.69 | 171 ± 12.14 | 173 ± 13.7 | 174 ± 15.9 | 178 ± 8.78 |
| Difference | | 11 | 14 | 26 | 25 | 24 | 20 |
| 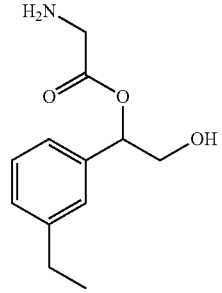 [SMILES: CCc1cccc(C(CO)OC(=O)CN)c1] Compound 23 | 196 ± 6.28 | 186 ± 6.39 | 187 ± 4.66 | 181 ± 9.15 | 183 ± 13.7 | 178 ± 15.9 | 178 ± 8.78 |
| Difference | | 10 | 9 | 15 | 13 | 18 | 18 |

TABLE 4-continued

Dynamic changes in SHR blood pressure after administration and difference before and after administration (SBP, mmHg) n = 8

| Group | Time after administration (h) | | | | | | |
|---|---|---|---|---|---|---|---|
| | 0 | 1 | 2 | 3 | 4 | 5 | 6 |
| 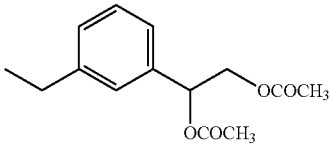 Compound 30 | 193 ± 4.39 | 189 ± 7.54 | 188 ± 3.69 | 185 ± 10.11 | 183 ± 9.66 | 188 ± 14.9 | 188 ± 8.64 |
| Difference | | 4 | 5 | 8 | 20 | 5 | 5 |
| 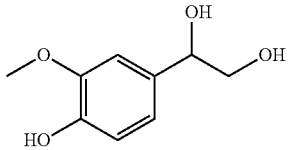 Compound 25 | 199 ± 7.09 | 191 ± 6.64 | 189 ± 7.77 | 186 ± 8.18 | 184 ± 4.56 | 187 ± 14.2 | 188 ± 5.55 |
| Difference | | 8 | 10 | 11 | 15 | 12 | 11 |

Example 14 Pulmonary Hypertension Test

This example studies therapeutic effects of the compounds of the invention on PAH model mice. During the experiment, SD rats were given hypobaric hypoxia and subcutaneous injection of monocrotaline to establish an animal model of PAH. The administration was continued during the establishment of PAH model mice. After the modeling was completed, the right ventricular pressure of the rat was measured and the heart and lung were preserved, which were used to calculate the hypertrophy index of the right ventricle and observe the morphological changes in the pulmonary blood vessels. Then, a single administration was given to the SHR spontaneous hypertension model rats, and the changes in blood pressure were monitored within 8 hours after administration.

The compound of the present invention was dissolved in physiological saline as a test drug. The methods of administration used in the experiment were gavage and inhalation. The positive drugs used in the experiment were selected according to different animal models and experimental requirements. The body weight of the rats was weighed every 3 days, and the growth of the rats was observed.

1. Therapeutic Effects of Oral Compound 1 on Animals with Hypoxic Pulmonary Hypertension 1) Purpose of Experiment An animal model of pulmonary hypertension in SD rats was established in a hypoxic and low-pressure environment, and compound 1 was administered by gavage at the same time for treatment. The rat pulmonary artery hemodynamics and right heart hypertrophy index RVHI were measured to determine whether compound 1 has effects of improving hypoxic pulmonary hypertension.

2) Experiment Animal and Experiment Method

SD rats (purchased from Shanghai Xipuer-Bikai Experimental Animal Co., Ltd.), male, weighing 180-200 g, were bred in an artificially controlled animal room with each 12 hours of light and darkness at a temperature of 20-25° C. and relative humidity of 50-60%, and allowed ad libitum to food and water. The rats were randomly divided into groups according to the experimental requirements, and kept separately in cages, with 3 to 4 rats per cage. All relevant operations of animal experiments are in compliance with the provisions of "Guidelines for the Management and Use of Laboratory Animals" of China.

The hypoxic PAH model was established by placing SD male rats in a fully-automatically regulated low-pressure hypoxic chamber (atmospheric pressure of about 50 kPa, oxygen concentration of 10%) for 8 hours a day for 28 days. The rats in the blank control group were kept in a normoxic environment.

The experimental rats of hypoxic PAH model were divided into 8 groups, namely blank control group, model group, Sidenafil (25 mg/kg) group, compound 1 (10 mg/kg) group, compound 1 (25 mg/kg) group, compound 1 (50 mg/kg) group, compound 1 (100 mg/kg) group, and compound 1 (200 mg/kg) group. The concentration in the parentheses of the group name represents the administration concentration of the compound or drug. In hypoxia-induced PAH experiments, Sidenafil is often used as a positive drug, which can reduce the pulmonary artery pressure in rats and reduce the right ventricular hypertrophy and vascular remodeling. In this experiment, 25 mg/kg of Sidenafil was used as the positive drug. Both the positive drugs Sidenafil and Compound 1 were dissolved in physiological saline and formulated into solutions of different concentrations according to different administration concentrations. The rats were continuously administered for 28 days with an administration volume of 5 ml/kg. Rats in the control and model groups were given the corresponding volume of physiological saline solution via gavage. The specific grouping can be found in Table 5.

After the administration was completed, the POWERLAB biological information acquisition and treatment system was started, and the right cardiac catheter filled with 0.2% heparin sodium (Beijing Solo Technology Co. Ltd.) in normal saline was connected to the pressure transducer and then zero-calibrationed for use. After 20% urethane (Shanghai Yuanye Biotechnology Co., Ltd.) solution was injected into the abdominal cavity of the rats for anesthesia, the right neck hair was shaved and the right jugular vein was isolated and exposed. The right heart catheter was inserted into the right jugular vein of the rat, entered the right atrium through the superior vena cava, and reached the right ventricle through the atrioventricular valve. After the typical right ventricular waveform appeared and stabilized for a while, the waveform was recorded, and then the pressure value was read by Powerlab biological information acquisition and processing system (ADInstruments).

After the pressure was measured, the catheter was taken out, and the rat was dissected immediately to take out the heart and lung tissues. The right ventricle (RV) and the left ventricle and interventricular septum (LV+S) were separated and weighed, and the right heart hypertrophy index RVHI=RV/(LV+S) was calculated. The lung lobe tissue from the right lower part of the lung was separated, soaked in 4% paraformaldehyde (Sigma) for about 1 week to prepare a paraffin section with a thickness of 3 μm, and then conducted to hematoxylin-eosin staining (Wuhan Guge Biotechnology Co., Ltd.). After the HE staining of the paraffin sections of the rat lung tissues in each group was completed, the sections were observed under an inverted microscope (Nikon TS100), and 5 pulmonary arteries were taken from each section and recorded under a 200× field of view. Image-pro plus 6.0 software was used to analyze the small pulmonary arteries with a diameter of 100-300 μm, and the percentage of the wall thickness to the outer diameter of the blood vessel (WT %) and the percentage of the wall area to the total area of the blood vessel (WA %) were calculated.

1 200 mg/kg: P<0.001, P<0.01). In the experiment, a positive control group of sildenafil was also set up (compared with the model group in RVSP: P<0.001, mRVP: P<0.01). It is suggested that when the dosages of AH001 were 100 mg/kg and 200 mg/kg and after intragastric administration for treatment for 28 days, the increase of pulmonary artery pressure in hypoxia-induced pulmonary hypertension rats can be improved.

(2) It can be seen from FIG. 1C that, in the hypoxic PAH model, the RV/(LV+S) value of model rats was significantly higher as compared with the normal rats (P<0.001), indicating that continuous low pressure and hypoxia can lead to remodeling and thickening of the right heart in SD rats. After different dosages of compound 1 were orally adminstered to treat hypoxia-induced rats for 28 days, it was found that when the dosages of compound 1 were 10 mg/kg, 25 mg/kg and 50 mg/kg, there was no significant decline in the RVHI of rats as compared with the model group. However, when the dosages of compound 1 were 100 mg/kg and 200 mg/kg, the hypertrophy of the right heart of rats was significantly improved compared with the model group (P<0.01, P<0.001). The positive drug sildenafil can improve the remodeling of the right ventricle and effectively reduce the value of RV/(LV+S) (P<0.001). It is suggested that when the dosages of compound 1 were 100 mg/kg and 200 mg/kg and after intragastric administration for treatment for 28 days,

TABLE 5

Grouping of hypoxic pulmonary hypertension model rats

| Group No. | Grouping | Number of rats | Mode of administration | Number of doses |
|---|---|---|---|---|
| 1 | Control group | 6 | Gavage | once a day |
| 2 | Model group | 6 | Gavage | once a day |
| 3 | Sidenafil (25 mg/kg) group | 6 | Gavage | once a day |
| 4 | Compound 1 (10 mg/kg) group | 6 | Gavage | once a day |
| 5 | Compound 1 (25 mg/kg) group | 6 | Gavage | once a day |
| 6 | Compound 1 (50 mg/kg) group | 6 | Gavage | once a day |
| 7 | Compound 1 (100 mg/kg) group | 6 | Gavage | once a day |
| 8 | Compound 1 (200 mg/kg) group | 6 | Gavage | once a day |

3) Experiment Results

Figure 2:
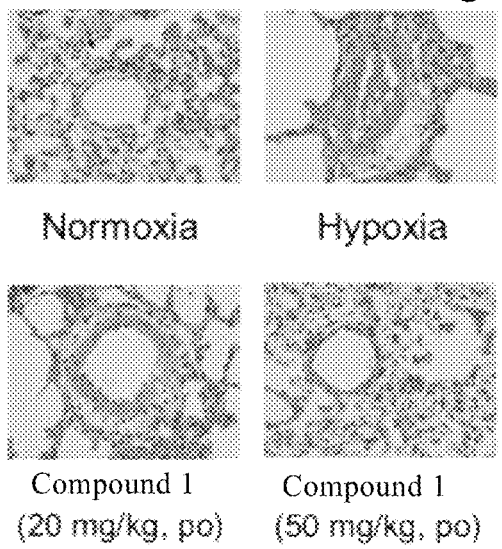
FIG. 2 shows reducing effects of orally administered compound 1 on the level of medium and small arteries hypertrophy in lung tissue of a low-oxygen pulmonary artery high-pressure rat.
Figure 2:
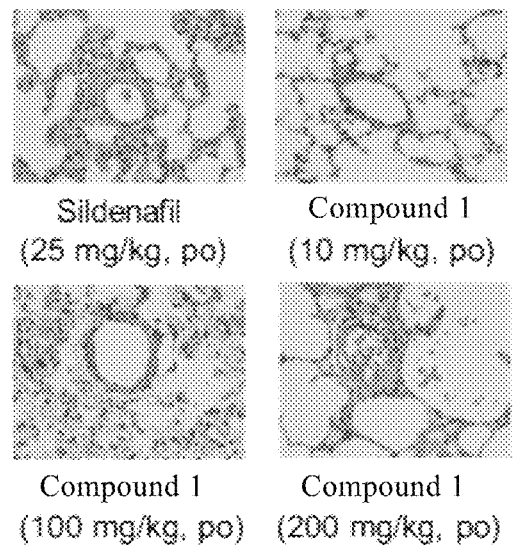

Experiment results are shown in FIGS. 1 and 2, wherein:

(1) It can be seen from Figure TA and FIG. 1B that, in the PAH model of indirect hypobaric hypoxia, there was significant difference between normal rats (average value of RVSP was 29.76±2.48 mmHg, and average value of mRVP was 8.16±1.45 mmHg) and model rats (average value of RVSP was 75.46±2.57 mmHg, and average value of mRVP was 26.12±2.37 mmHg), and P<0.001, indicating that the PAH model was successfully established in this experiment. When different dosages of compound 1 were orally administered to treat hypoxia-induced rats for 28 days, it was found that when the doses of compound 1 were 10 mg/kg, 25 mg/kg, and 50 mg/kg, there was no significant drop in the rats' pulmonary vascular pressure as compared with the model group. However, when the dosages of compound 1 were 100 mg/kg and 200 mg/kg, the RVSP and mRVP of rats were significantly lower than those of the untreated model group (compound 1 100 mg/kg: P<0.01, P<0.05; compound the increase of pulmonary artery pressure in hypoxia-induced pulmonary hypertension rats can be improved.

(3) It can be seen from FIG. 1D and FIG. 2 that long-term hypoxia significantly thickened the small pulmonary arterioles in the model group, and the medium thickness (2×MT/ED) ratio of the small pulmonary arteries increased significantly (P<0.001 vs. Control). Compared with the model group, when the dosage of compound 1 was 10 mg/kg, 25 mg/kg and 50 mg/kg, the pulmonary vascular remodeling in rats was not alleviated. However, when the dosages of compound 1 were 100 mg/kg and 200 mg/kg, the medium thickness ratio of rats was significantly improved compared with the model group (P<0.05, P<0.001). It is suggested that when the dosages of compound 1 were 100 mg/kg and 200 mg/kg and after intragastric administration for treatment for 28 days, hypoxia-induced hypertrophy of small arteries in lung tissue of rats with pulmonary hypertension can be alleviated.

TABLE 6

Experimental results of compound 1 and series of compounds on hypoxic pulmonary hypertension model rats

| Grouping of experiment animals | RVSP/ mmHg | mPAP/ mmHg | RVHI | 2 × MT/ED |
| --- | --- | --- | --- | --- |
| Control group | 29.76 ± 2.48 | 8.16 ± 1.45 | 0.221 ± 0.045 | 0.189 ± 0.016 |
| Model group | 75.46 ± 2.57 | 26.12 ± 2.37 | 0.462 ± 0.048 | 0.358 ± 0.027 |
| Sildenafil group (25 mg/kg, po) | 50.12 ± 2.96 | 14.34 ± 2.48 | 0.240 ± 0.028 | 0.238 ± 0.018 |
| Compound 1 group (10 mg/kg, po) | 70.28 ± 4.64 | 25.26 ± 3.46 | 0.467 ± 0.030 | 0.361 ± 0.020 |
| Compound 1 group (25 mg/kg, po) | 71.34 ± 2.12 | 22.36 ± 1.78 | 0.472 ± 0.026 | 0.323 ± 0.022 |
| Compound 1 group (50 mg/kg, po) | 67.46 ± 4.28 | 21.66 ± 3.28 | 0.456 ± 0.019 | 0.304 ± 0.021 |
| Compound 1 group (100 mg/kg, po) | 59.12 ± 2.12 | 15.89 ± 1.12 | 0.301 ± 0.017 | 0.266 ± 0.014 |
| Compound 1 group (200 mg/kg, po) | 54.38 ± 2.98 | 15.21 ± 1.92 | 0.254 ± 0.022 | 0.241 ± 0.011 |
| Compound 7 (200 mg/kg, po) | 62.78 ± 3.41 | 16.64 ± 2.08 | 0.261 ± 0.037 | 0.291 ± 0.023 |
| Compound 8 (200 mg/kg, po) | 62.50 ± 2.91 | 17.19 ± 3.65 | 0.296 ± 0.027 | 0.277 ± 0.022 |
| Compound 5 (200 mg/kg, po) | 60.29 ± 3.87 | 15.76 ± 2.71 | 0.271 ± 0.038 | 0.270 ± 0.012 |
| Compound 16 (200 mg/kg, po) | 65.83 ± 3.26 | 18.60 ± 3.60 | 0.365 ± 0.031 | 0.289 ± 0.030 |

TABLE 6-continued

Experimental results of compound 1 and series of compounds on hypoxic pulmonary hypertension model rats

| Grouping of experiment animals | RVSP/ mmHg | mPAP/ mmHg | RVHI | 2 × MT/ED |
|---|---|---|---|---|
| 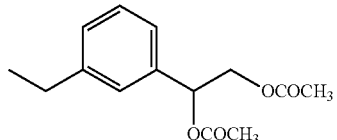<br>Compound 30<br>(200 mg/kg, po) | 62.14 ± 3.35 | 16.03 ± 5.35 | 0.303 ± 0.0632 | 0.287 ± 0.025 |

2. Therapeutic Effects of Oral Administration of the Compound of the Present Invention on Animals with Monocrotaline-Induced Pulmonary Hypertension 1) Purpose of Experiment Monocrotaline (MCT) was subcutaneously injected to establish an animal model of pulmonary hypertension in SD rats. At the same time, compound 1 was given by gavage for treatment. The pulmonary artery hemodynamics and right heart hypertrophy index RVHI of the rates were detected to determine whether the oral administration of compound 1 has effects of improving Monocrotaline induces pulmonary hypertension.

2) Experiment Animals and Experiment Methods

SD rats (purchased from Shanghai Xipuer-Bikai Experimental Animal Co., Ltd.), male, weighing 180-200 g, were bred in an artificially controlled animal room with each 12 hours of light and darkness at a temperature of 20-25° C. and relative humidity of 50-60%, and allowed ad libitum to food and water. The rats were randomly divided into groups according to the experimental requirements, and kept separately in cages, with 3 to 4 rats per cage. All relevant operations of animal experiments are in compliance with the provisions of "Guidelines for the Management and Use of Laboratory Animals" of China.

During the experiment, SD rats were randomly divided into 4 groups: blank control group, pulmonary hypertension model group, Selexipag (1 mg/kg) treatment group and compound 1 (100 mg/kg) group with 6 rats in each group, and the concentration in brackets represents the administration concentration of the compound, in which Selexipag is a new oral long-acting prostacyclin receptor agonist discovered and synthesized by Japan New Drug Co., Ltd. On the first day of the experiment, normal saline was injected subcutaneously into the back of neck of rats in the blank control group, and monocrotaline (Chengdu Purifa Biotechnology Co., Ltd.) solution was injected in the rats in other groups at a dosage of 60 mg/kg. Both the positive drug, Selexipag and Compound 1 were administered by gavage. Selexipag and compound 102 were dissolved in 0.5% CMC-Na solution. The rats were continuously administered for 21 days with a volume of 5 mg/kg. The rats in the control and model groups were given the corresponding volume of CMC-Na solution by gavage. Specific groupings can be found in Table 7.

After the administration, the pulmonary vascular hemodynamics and RVHI was determined according to the same experiment method as that in Example 1.

TABLE 7

Grouping of Monocrotaline Induced Pulmonary Hypertension Model Rats (Oral)

| Group No. | Grouping | Number of rats | Administration mode | Number of administration |
|---|---|---|---|---|
| 1 | Control group | 6 | gavage | once a day |
| 2 | Model group | 6 | gavage | once a day |
| 3 | Selexipag (1 mg/kg) group | 6 | gavage | Twice a day |
| 4 | Compound 1 (100 mg/kg) group | 6 | gavage | once a day |

Figure 3:
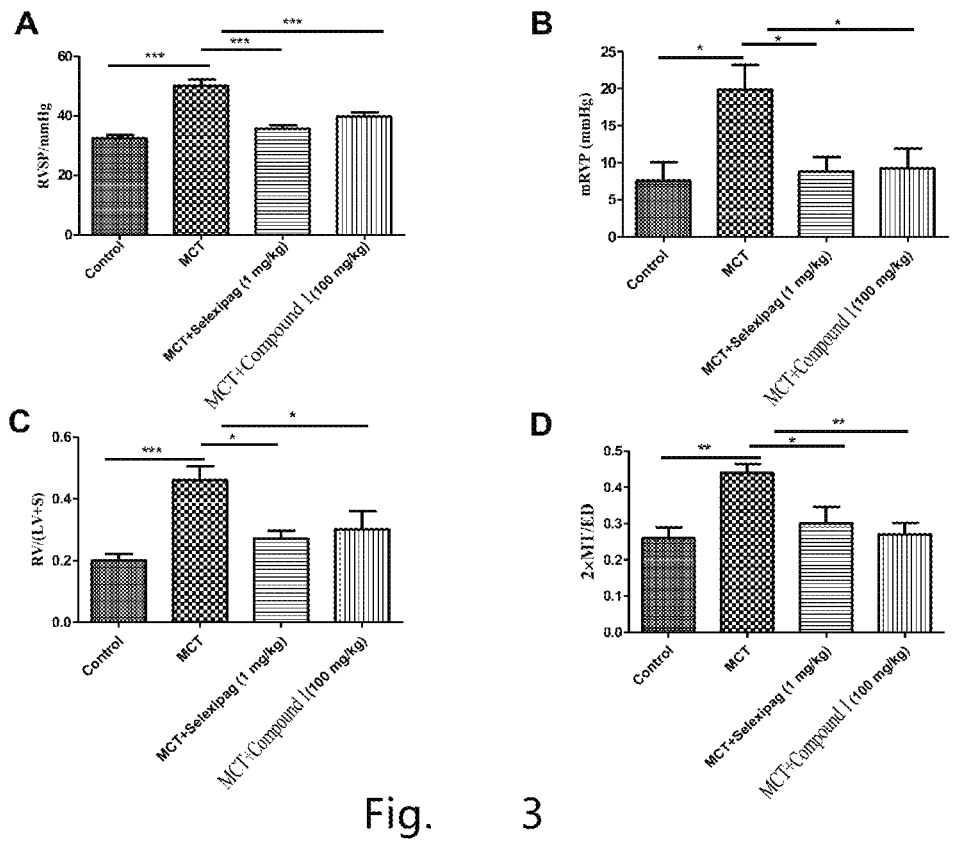
FIG. 3 shows therapeutic effect of orally administered compound 1 on monocrotaline-induced pulmonary hypertension animal model.

3) Experiment Results (1) It can be seen from FIG. 3A and FIG. 3B that the RVSP and mRVP of the blank control group were 32.43±2.78 mmHg and 7.56±2.52 mmHg, respectively. After pulmonary hypertension was induced by monocrotaline, the RVSP and mPAP of rats increased (P<0.001, P<0.05). After treatment with compound 1 (100 mg/kg, po), the pulmonary vascular pressure of rats was higher than that of the blank control group, but the RVSP and mRVP were significantly lower than those of the untreated model group (P<0.001, P<0.05). In the experiment a selexipag positive drug control group (compared with the model group RVSP: P<0.001, mRVP: P<0.05) was also set. It was suggested that when the dosage of compound 1 was 100 mg/kg and after intragastric administration for treatment for 21 days, the increase of pulmonary artery pressure in Monocrotaline-induced pulmonary hypertension rats can be improved.

(2) It can be seen from FIG. 3C that the RVHIs of the blank control group and the model group were 0.20±0.021 and 0.46±0.045, respectively, and the right heart hypertrophy index of the model group was significantly increased (P<0.001). After treatment with compound 1 (100 mg/kg, po), the RVHI of rats was 0.31±0.059, which was significantly lower than that of the untreated model group (P<0.05). At the same time, the right heart hypertrophy index of the positive control drug selexipag treatment group was 0.27±0.026, which was significantly lower than that of the model group (P<0.05). It is suggested that when the dose of compound 1 is 100 mg/kg and after intragastric administration for treatment for 21 days, the right heart hypertrophy caused by pulmonary hypertension can be relieved.

Figure 4:
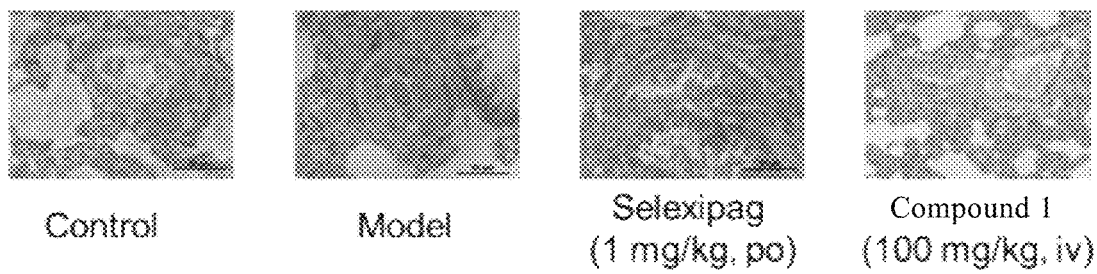
FIG. 4 shows reducing effects of orally administered compound 1 on the level of medium and small arteries hypertrophy in pulmonary tissues of a monocrotaline-induced pulmonary artery high-pressure rat.

(3) It can be seen from FIG. 3D and FIG. 4 that in the pulmonary hypertension model rats modeled by monocrotaline, the arterioles were significantly thickened, and the media thickness (2×MT/ED) ratio of the pulmonary arterioles was significantly increased (P<0.01). Compared with the model group, the pathological changes of arteriolar hypertrophy in the lung tissue of rats in the compound 1 (100 mg/kg, po) group were significantly reduced (P<0.01). In the experiment, a selexipag positive drug control group was also set. After intervention with selexipag for 21 days, the pulmonary arteriole hypertrophy was significantly reduced (P<0.05 vs. Model). It is suggested that when the dosage of compound 1 is 100 mg/kg and after intragastric administration for treatment for 21 days, the arterial hypertrophy in the lung tissue of rats with monocrotaline-induced pulmonary hypertension can be reduced.

TABLE 8

Experiment results of orally administered Compound 1 and series Compounds for treating MCT-PAH Rats

| Grouping of experiment animals | RVSP/ mmHg | mPAP/ mmHg | RVHI | 2 × MT/ED |
|---|---|---|---|---|
| Control group | 32.43 ± 2.78 | 7.56 ± 2.52 | 0.20 ± 0.021 | 0.26 ± 0.059 |
| Model group | 50.06 ± 5.28 | 19.87 ± 3.35 | 0.46 ± 0.045 | 0.39 ± 0.024 |
| selexipag group (1 mg/kg, po) | 35.67 ± 2.89 | 8.78 ± 1.98 | 0.27 ± 0.026 | 0.30 ± 0.086 |
| Compound 1 group (100 mg/kg, po) [1-(3-ethylphenyl)ethane-1,2-diol] | 39.72 ± 3.46 | 9.21 ± 2.69 | 0.31 ± 0.059 | 0.27 ± 0.062 |
| Compound 7 (100 mg/kg, po) [1-(3-fluorophenyl)ethane-1,2-diol] | 42.31 ± 2.78 | 15.67 ± 2.70 | 0.33 ± 0.058 | 0.27 ± 0.045 |
| Compound 8 (100 mg/kg, po) [1-(3-methoxyphenyl)ethane-1,2-diol] | 45.97 ± 3.49 | 16.47 ± 3.07 | 0.33 ± 0.037 | 0.31 ± 0.052 |
| Compound 5 (100 mg/kg, po) [1-(2-ethylphenyl)ethane-1,2-diol] | 44.32 ± 2.12 | 15.76 ± 2.71 | 0.35 ± 0.048 | 0.29 ± 0.054 |
| Compound 16 (100 mg/kg, po) [glucoside of 1-(3-ethylphenyl)ethane-1,2-diol] | 48.89 ± 6.64 | 16.74 ± 3.08 | 0.320 ± 0.031 | 0.32 ± 0.066 |

TABLE 8-continued

Experiment results of orally administered Compound 1 and series Compounds for treating MCT-PAH Rats

| Grouping of experiment animals | RVSP/ mmHg | mPAP/ mmHg | RVHI | 2 × MT/ED |
|---|---|---|---|---|
| 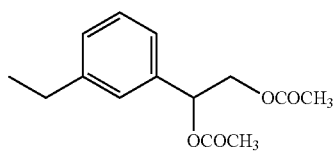<br>Compound 30<br>(100 mg/kg, po) | 44.38 ± 2.89 | 16.21 ± 1.29 | 0.245 ± 0.032 | 0.31 ± 0.021 |

3. Therapeutic Effects of Atomized Administered Compound 1 on Monocrotaline-Induced Pulmonary Hypertension Animals 1) Purpose of Experiment A pulmonary hypertension animal model of SD rats was established by subcutaneous injection of monocrotaline (MCT). The compound 1 was administered by aerosol inhalation for treatment. The pulmonary artery hemodynamics and right heart hypertrophy index RVHI of rats were tested to determine whether compound 1 administered by aerosol inhalation has effects of improving monocrotaline-induced pulmonary hypertension.

2) Experiment Animal and Experiment Method

SD rats (purchased from Shanghai Xipuer-Bikai Experimental Animal Co., Ltd.), male, weighing 180-200 g, were bred in an artificially controlled animal room with each 12 hours of light and darkness at a temperature of 20-25° C. and relative humidity of 50-60%, and allowed ad libitum to food and water. The rats were randomly divided into groups according to the experimental requirements, and kept separately in cages, with 3 to 4 rats per cage. All relevant operations of animal experiments are in compliance with the provisions of "Guidelines for the Management and Use of Laboratory Animals" of China.

In the second experiment, the rats were divided into 5 groups, namely the control group, model group, positive control Tyvaso (1.62 μg/kg) group, compound 1 (10 mg/kg) group and compound 1 (30 mg/kg) group. On the first day of the experiment, normal saline was injected subcutaneously into the back of the neck of the rats in the blank control group, and monocrotaline (Chengdu Purifa Biotechnology Co., Ltd.) solution was injected in the other groups at a dosage of 60 mg/kg. Compound 1 and Tyvaso were administered by aerosol inhalation, that is, the compound was firstly dissolved in physiological saline, and then the solution was prepared into an aerosol with a nebulizer to be inhaled into the mouth and nose of rats. The rats in the control group and the model group only inhaled an aerosol made of physiological saline. The rats were continuously administered for 28 days, and the concentration in the parentheses of the group name represents the administered concentration of the compound. Specific groupings can be found in Table 9. After the administration, the pulmonary vascular hemodynamics and RVHI were determined in the same way as the experiment method in Example 1.

TABLE 9

Groupings of Model Rat with monocrotaline-induced pulmonary hypertension (Aerosol Inhalation)

| Group No. | Grouping | Number of rats | Administration mode | Number of administration |
|---|---|---|---|---|
| 1 | Control group | 6 | Aerosol Inhalation | once a day |
| 2 | Model group | 6 | Aerosol Inhalation | once a day |
| 4 | Tyvaso (1.62 μg/kg) group | 6 | Aerosol Inhalation | Four times a day |
| 5 | Compound 1 (10 mg/kg) group | 6 | Aerosol Inhalation | once a day |
| 6 | Compound 1 (30 mg/kg) group | 6 | Aerosol Inhalation | once a day |

Figure 5:
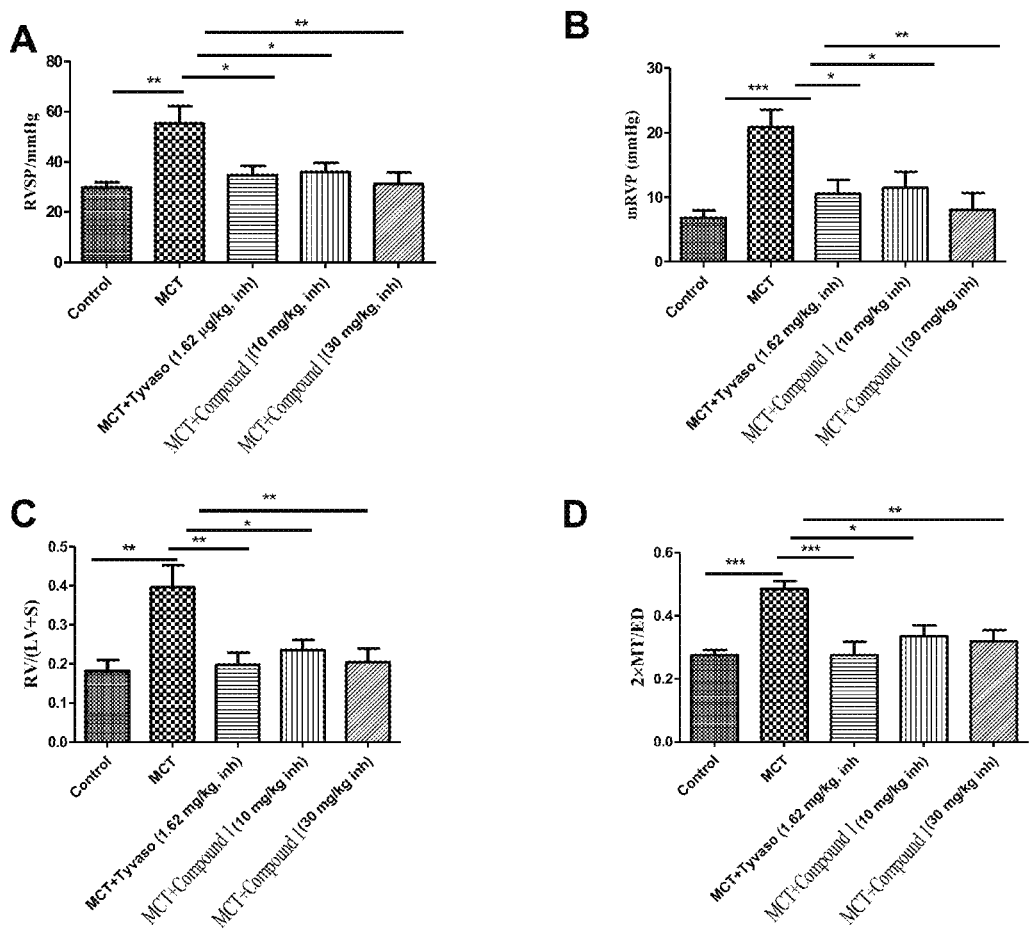
FIG. 5 shows therapeutic effects of compound 1 administered through atomization on a monocrotaline-induced pulmonary hypertension animal models.

3) Experiment Results (1) It can be seen from FIG. 5A and FIG. 5B that the RVSP and mRVP of the blank control group were 29.78±2.12 mmHg and 6.78±1.15 mmHg, respectively. After pulmonary hypertension was induced by monocrotaline, the RVSP and mPAP of rats increased (P<0.01, P<0.001). After compound 1 (10 mg/kg and 30 mg/kg) was administered by aerosol inhalation for treatment, the pulmonary vascular pressure of rats was higher than that of the blank control group, however, the RVSP was significantly lower than that of the untreated model group (P<0.05, P<0.01). While after compound 1 was administered by aerosol inhalation for treatment, mRVP also showed the same trend. In the experiment a Tyvaso positive drug control group (compared with the model group RVSP: P<0.05, mRVP: P<0.05) was also set. It was suggested that when compound 1 was administered by aerosol inhalation at the dosages of 10 mg/kg and 30 mg/kg, the increase of pulmonary artery pressure in rats with monocrotaline-induced pulmonary hypertension can be improved.

(2) It can be seen from FIG. 5C that the RVHI of the rats in the blank control group of model group were 0.182±0.028 mmHg and 0.396±0.056 mmHg, respectively. The right heart hypertrophy index in the model group was significantly increased (P<0.01). After compound 1 (10 mg/kg and 30 mg/kg) was administered by aerosol inhalation for treatment, the RVHIs of the two groups of rats decreased to 0.235±0.026 and 0.204±0.035, respectively, which was significantly lower than that of the untreated model group (P<0.05, P<0.01). At the same time, the right ventricular hypertrophy index of the positive control drug Tyvaso treatment group was 0.197±0.031, which was significantly lower than that of the model group (P<0.01). It was suggested that when compound 1 was administered by aerosol inhalation at the dosages of 10 mg/kg and 30 mg/kg, the right heart hypertrophy caused by pulmonary hypertension can be relieved.

Figure 6:
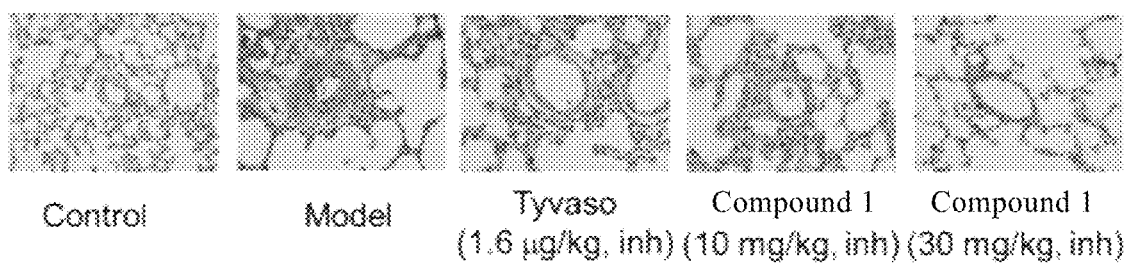
FIG. 6 shows reducing effect of oral compound 1 administered through atomization on the level of medium and small arteries hypertrophy in pulmonary tissues of a monocrotaline-induced pulmonary artery high-pressure rat.

(3) From FIG. 5D and FIG. 6, it can be seen that after monocrotaline modelling, the small arteries of the rats in the pulmonary hypertension model group were significantly thickened, and the media thickness ratio of the small pulmonary arteries (2×MT/ED) increased significantly (P<0.01). Compared with the model group, after compound 1 (10 mg/kg and 30 mg/kg) was administered by aerosol inhalation for treatment, pathological changes of pulmonary arteriole hypertrophy in lung tissues of rats were significantly reduced (P<0.05, P<0.01). In the experiment, a Tyvaso positive drug control group was also set. After Tyvaso was administered by inhalation for 21 days, pulmonary arteriole hypertrophy was significantly reduced (P<0.001 vs. Model). It was suggested that when compound 1 was administered by aerosol inhalation at the dosages of 10 mg/kg and 30 mg/kg, the hypertrophy of small arteries in the lung tissue of rats with monocrotaline-induced pulmonary hypertension was reduced.

TABLE 10

Experiment Results of compound 1 and series compounds administered by aerosol inhalation for treating MCT-PAH Rats

| Grouping of experiment animals | RVSP/ mmHg | mPAP/ mmHg | RVHI | 2 × MT/ED |
|---|---|---|---|---|
| Control group | 29.78 ± 2.12 | 6.78 ± 1.15 | 0.182 ± 0.028 | 0.275 ± 0.017 |
| Model group | 55.23 ± 6.94 | 20.88 ± 2.68 | 0.396 ± 0.056 | 0.485 ± 0.025 |
| Tyvaso group (1.62 μg/kg, inh) | 34.61 ± 3.69 | 10.54 ± 2.14 | 0.197 ± 0.031 | 0.275 ± 0.042 |
| Compound 1 (10 mg/kg, inh) | 35.92 ± 3.74 | 11.46 ± 2.48 | 0.235 ± 0.026 | 0.335 ± 0.034 |
| Compound 1 (30 mg/kg, inh) | 31.18 ± 4.62 | 8.06 ± 2.59 | 0.204 ± 0.035 | 0.319 ± 0.035 |
| Compound 7 (30 mg/kg, inh) | 44.61 ± 2.96 | 12.45 ± 2.41 | 0.267 ± 0.013 | 0.375 ± 0.024 |
| Compound 8 (30 mg/kg, inh) | 45.92 ± 3.47 | 14.16 ± 3.84 | 0.306 ± 0.027 | 0.353 ± 0.043 |
| Compound 5 (30 mg/kg, inh) | 40.18 ± 4.62 | 11.06 ± 2.95 | 0.324 ± 0.053 | 0.390 ± 0.038 |
| Compound 16 (30 mg/kg, inh) | 41.44 ± 2.03 | 14.76 ± 1.98 | 0.290 ± 0.054 | 0.357 ± 0.032 |

TABLE 10-continued

Experiment Results of compound 1 and series compounds administered by aerosol inhalation for treating MCT-PAH Rats

| Grouping of experiment animals | RVSP/ mmHg | mPAP/ mmHg | RVHI | 2 × MT/ED |
|---|---|---|---|---|
| Compound 30 (30 mg/kg, inh) | 46.04 ± 3.27 | 16.00 ± 3.44 | 0.273 ± 0.043 | 0.402 ± 0.034 |

All documents mentioned in this application are incorporated herein by reference, as if each document were individually incorporated by reference. It should also be understood that various changes or modifications may be made by those skilled in the art upon reading the above teachings of the invention, which are likewise within the scope defined by the claims appended hereto.

The invention claimed is:

1. A method for preventing or treating a hypertension or hypertension related disease or pulmonary hypertension or pulmonary hypertension related disease, comprising administering to a subject in need thereof a therapeutically effective amount of a compound of formula I, wherein the compound is

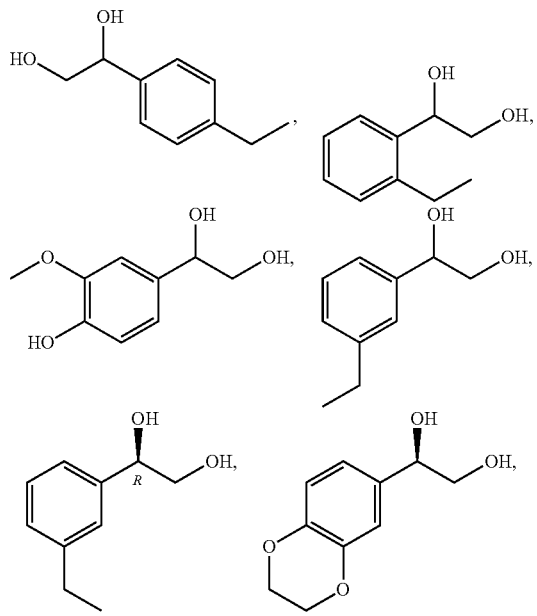

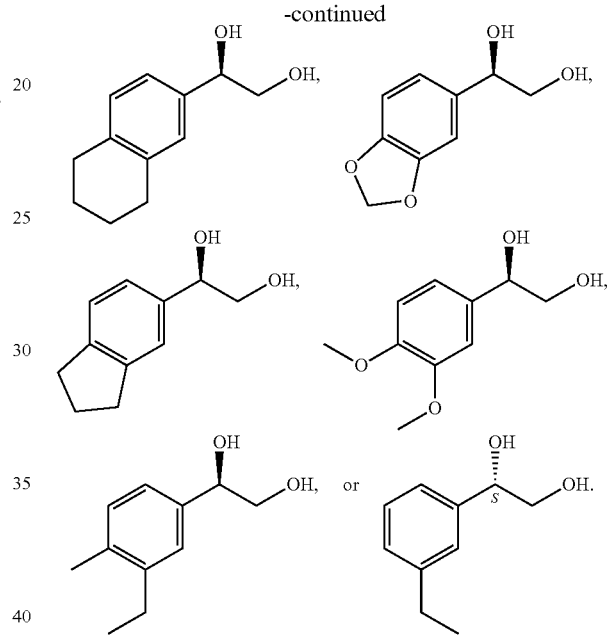

2. The method of claim 1, wherein the hypertension-related disease is selected from the group consisting of cerebral apoplexy, hypertension heart disease, hypertension nephropathy, hypertension fundus lesions and retinal lesions, and hypertension lower limb ischemia; and the pulmonary hypertension-related disease is selected from the group consisting of idiopathic pulmonary hypertension, lung-derived heart disease, plateau heart disease, cardiovascular disease, pulmonary obstruction, fibrotic disorders, and urinary system disorders.

3. The method of claim 2, wherein the cerebral apoplexy is cerebral hemorrhage or cerebral ischemia.

* * * * *